US009810637B2

(12) United States Patent
Geddes

(10) Patent No.: US 9,810,637 B2
(45) Date of Patent: *Nov. 7, 2017

(54) PLASMONIC ELECTRICITY

(75) Inventor: Chris D. Geddes, Bel-Air, MD (US)

(73) Assignee: UNIVERSITY OF MARYLAND, BALTIMORE COUNTY, Baltimore, MD (US)

(*) Notice: Subject to any disclaimer, the term of this patent is extended or adjusted under 35 U.S.C. 154(b) by 991 days.

This patent is subject to a terminal disclaimer.

(21) Appl. No.: 13/515,542

(22) PCT Filed: Dec. 14, 2010

(86) PCT No.: PCT/US2010/060174
§ 371 (c)(1),
(2), (4) Date: Nov. 7, 2012

(87) PCT Pub. No.: WO2011/081896
PCT Pub. Date: Jul. 7, 2011

(65) Prior Publication Data
US 2013/0059316 A1 Mar. 7, 2013

Related U.S. Application Data

(60) Provisional application No. 61/286,331, filed on Dec. 14, 2009.

(51) Int. Cl.
*G01N 21/76* (2006.01)
*G01N 21/64* (2006.01)

(52) U.S. Cl.
CPC .......... *G01N 21/76* (2013.01); *G01N 21/645* (2013.01); *G01N 2458/30* (2013.01)

(58) Field of Classification Search
CPC .......... G11B 5/33; G11B 5/127; G01N 23/00; H01L 31/00
See application file for complete search history.

(56) References Cited

U.S. PATENT DOCUMENTS

| 5,017,009 A | 5/1991 | Schutt et al. |
| 5,449,918 A | 9/1995 | Krull et al. |
| 5,841,143 A | 11/1998 | Tuma et al. |

(Continued)

FOREIGN PATENT DOCUMENTS

| JP | 2009-058474 | 3/2009 |
| WO | WO89/09408 | 10/1989 |

(Continued)

OTHER PUBLICATIONS

Aslan, K.; Geddes, C. D., Microwave-accelerated metal-enhanced fluorescence: Platform technology for ultrafast and ultrabright assays, *Analytical Chemistry* 2005, 77, 8057-8067.

(Continued)

*Primary Examiner* — Rebecca Martinez
(74) *Attorney, Agent, or Firm* — Marianne Fuierer; Moore & Van Allen, PLLC

(57) ABSTRACT

The present invention relates to detection systems and methods that detect fluorescence, luminescence, chemiluminescence or phosphorescence signatures in the form of an electrical signal conducted and emitted from metallic containing surfaces. Thus, the present invention provides for detecting fluorescence digitally and directly without the need for expensive detectors.

16 Claims, 24 Drawing Sheets

(56) References Cited

U.S. PATENT DOCUMENTS

| | | | |
|---|---|---|---|
| 5,866,433 | A | 2/1999 | Schalkhammer et al. |
| 7,095,502 | B2 | 8/2006 | Lakowicz et al. |
| 7,253,452 | B2 | 8/2007 | Steckel et al. |
| 7,348,182 | B2 | 3/2008 | Martin et al. |
| 7,351,590 | B2 | 4/2008 | Martin |
| 7,400,397 | B2 | 7/2008 | Lakowicz et al. |
| 7,648,834 | B2 | 1/2010 | Moore |
| 7,718,445 | B2 | 5/2010 | Martin |
| 7,718,804 | B2 | 5/2010 | Geddes et al. |
| 7,732,215 | B2 | 6/2010 | Geddes et al. |
| 7,939,333 | B2 | 5/2011 | Geddes et al. |
| 8,008,067 | B2 | 8/2011 | Geddes et al. |
| 8,034,633 | B2 | 10/2011 | Geddes |
| 8,075,956 | B2 | 12/2011 | Geddes et al. |
| 8,101,424 | B2 | 1/2012 | Geddes |
| 8,114,598 | B2 | 2/2012 | Geddes et al. |
| 8,182,878 | B2 | 5/2012 | Geddes et al. |
| 8,318,087 | B2 | 11/2012 | Geddes |
| 8,338,602 | B2 | 12/2012 | Geddes et al. |
| 2003/0228682 | A1 | 12/2003 | Lakowicz et al. |
| 2005/0053974 | A1 | 3/2005 | Lakowicz et al. |
| 2005/0236033 | A1 | 10/2005 | Lawandy |
| 2006/0141268 | A1* | 6/2006 | Kalkan et al. ............. 428/446 |
| 2006/0147927 | A1 | 7/2006 | Geddes et al. |
| 2006/0192115 | A1* | 8/2006 | Thomas et al. ............ 250/306 |
| 2007/0042396 | A1* | 2/2007 | Park et al. ................ 435/6 |
| 2007/0115474 | A1 | 5/2007 | Chaton et al. |
| 2007/0269826 | A1 | 11/2007 | Geddes et al. |
| 2007/0278607 | A1 | 12/2007 | Gruhlke et al. |
| 2007/0289623 | A1* | 12/2007 | Atwater .................. 136/252 |
| 2008/0161201 | A1* | 7/2008 | Ootsubo et al. .......... 506/15 |
| 2008/0215122 | A1 | 9/2008 | Geddes et al. |
| 2008/0285040 | A1 | 11/2008 | Fourkas et al. |
| 2009/0022766 | A1 | 1/2009 | Geddes et al. |
| 2009/0325199 | A1 | 12/2009 | Geddes et al. |
| 2010/0062545 | A1 | 3/2010 | Geddes et al. |
| 2010/0209937 | A1 | 8/2010 | Geddes et al. |
| 2010/0297016 | A1 | 11/2010 | Geddes et al. |
| 2011/0020946 | A1 | 1/2011 | Geddes |
| 2011/0136154 | A1 | 6/2011 | Geddes |
| 2011/0207236 | A1 | 8/2011 | Geddes |
| 2012/0021443 | A1 | 1/2012 | Geddes |
| 2012/0028270 | A1 | 2/2012 | Geddes |
| 2012/0091349 | A1 | 4/2012 | Geddes |
| 2012/0107952 | A1 | 5/2012 | Geddes et al. |
| 2012/0142552 | A1 | 6/2012 | Geddes et al. |
| 2012/0238035 | A1 | 9/2012 | Geddes |
| 2012/0282630 | A1 | 11/2012 | Geddes |
| 2013/0020503 | A1 | 1/2013 | Geddes |

FOREIGN PATENT DOCUMENTS

| | | |
|---|---|---|
| WO | WO2004/024191 | 3/2004 |
| WO | WO2008121097 | 10/2008 |
| WO | WO2009134527 | 11/2009 |

OTHER PUBLICATIONS

Aslan, K.; Zhang, Y.; Hibbs, S.; Baillie, L.; Previte, M. J.; Geddes, C. D., Microwave-accelerated metal-enhanced fluorescence: application to detection of genomic and exosporium anthrax DNA in <30 seconds, *Analyst* 2007, 132, 1130-1138.

Aslan, K., Leonenko, Z., Lakowicz. J.R., Geddes, C.D., Annealed silver-island films for applications in metal-enhanced fluorescence: Interpretation in terms of radiating plasmons, J. Fluoresc. 2005, 15, 643-654.

Aslan, K.; Gryczynski, I.; Malicka, J.; Matveeva, E.; Lakowicz, J. R.; Geddes, C. D, Metal-enhanced fluorescence: an emerging tool in biotechnology, *Current Opinion in Biotechnology* 2005, 16, 55-62.

Aslan, K.; Lakowicz, J. R.; Szmacinski, H.; Geddes, C. D., Enhanced ratiometric pH sensing using SNAFL-2 on silver island films: Metal-enhanced fluorescence sensing, *Journal of Fluorescence* 2005, 15, 37-40.

Aslan, K.; Geddes, C. D., Microwave-accelerated Metal-enhanced Fluorescence (MAMEF): Application to ultra fast and sensitive clinical assays, *Journal of Fluorescence* 2006, 16, 3-8.

Aslan, K.; Holley, P.; Geddes, C. D., Microwave-Accelerated Metal-Enhanced Fluorescence (MAMEF) with silver colloids in 96-well plates: Application to ultra fast and sensitive immunoassays, High Throughput Screening and drug discovery, *Journal of Immunological Methods* 2006, 312, 137-147.

Collings, F. B.; Vaidya, V. S. : Novel technologies for the discovery and quantitation of biomarkers of toxicity, *Toxicology* 2008, 245, 167-174.

Enander, K.; Choulier, L.; Olsson, A. L.; Yushchenko, D. A.; Kanmert, D.; Klymchenko, A. S.; Demchenko, A. P.; Mely, Y.; Altschuh, D., A peptide-based, ratiometric biosensor construct for direct fluorescence detection of a protein analyte, *Bioconjug Chem* 2008.

Geddes, C. D.; Lakowicz, J. R., Metal-enhanced fluorescence, *Journal of Fluorescence* 2002, 12, 121-129.

Gould, R. K.; Coakley, W. T.; Grundy, M. A., Upper Sound Pressure Limits on Particle Concentration in Fields of Ultrasonic Standing-Wave At Megahertz Frequencies, *Ultrasonics* 1992, 30, 239-244.

Lofas, S.; Malmqvist, M.; Ronnberg, I.; Stenberg, E.; Liedberg, B.; Lundstrom, I., Bioanalysis With Surface-Plasmon Resonance, *Sensors and Actuators B-Chemical* 1991, 5, 79-84.

Matveeva, E.; Malicka, J.; Gryczynski, I.; Gryczynski, Z.; Lakowicz, J. R., Multi-wavelength immunoassays using surface plasmon-coupled emission *Biochem Biophys Res Commun* 2004, 313, 721-726.

Matveeva, E.; Gryczynski, Z.; Gryczynski, I.; Malicka, J.; Lakowicz, J. R., Myoglobin immunoassay utilizing directional surface plasmon-coupled emission, *Analytical Chemistry* 2004, 76, 6287-6292.

Neppiras, E. A., Acoustic Cavitation, *Phys. Rep.* 1980, 61, 159-251.

Suslick, K. S.; Flannigan, D. J., Inside a collapsing bubble: Sonoluminescence and the conditions during cavitation, *Annu Rev Phys Chem* 2008, 59, 659-683.

Schultz, E.; Galland, R.; Du Bouetiez, D.; Flahaut, T.; Planat-Chretien, A.; Lesbre, F.; Hoang, A.; Volland, H.; Perraut, F., A novel fluorescence-based array biosensor: Principle and application to DNA hybridization assays, *Biosens Bioelectron* 2008, 23, 987-994.

Suslick, K. S., Sonochemistry, Science 1990, 247, 1439-1445.

Taipa, M. A., Immunoassays: Biological tools for high throughput screening and characterisation of combinatorial libraries, *Comb Chem High Throughput Screen* 2008, 11, 325-335.

Thornycroft, L. H.; Barnaby, S. W., Torpedo-Boat Destroyers, *Min. Proc. Inst. Chem. Eng*, 1895, 122 51-69.

G. Bauer, F. Pittner and Th. Schalkhammer, Metal Nano-Cluster Biosensors, Mikrochim Acta 131, 107-114 (1999).

Th. Schalkhammer, Metal Nano Clusters as Transducers for Bioaffinity Interactions, Monatshefte für Chemie 129, 1067-1092 (1998).

Y. Zhang et al., Metal-enhanced fluorescence form copper substrates, Applied Physics Letters, Apr. 25, 2007, vol. 90, pp. 173116_1-173116_3.

Cannone, F. et al. Voltage Regulation of Fluorescence Emission of Single Dyes Bound to Gold Nanoparticles, *Nano Letters*, Apr. 1, 2007, vol. 7, No. 4, pp. 1070-1075.

Hagglund, C. et al. Enhanced charge carrier generation in dye sensitized solar cells by nanoparticle plasmons, *Applied Physics Letters, American Institute of Physics*, Jan. 4, 2008, vol. 92, No. 1, pp. 13113-13113.

Homola, J. et al. Surface plasmon resonance sensors: review, *Sensors and Actuators B: Chemical: International Journal Devoted to Research and Development of Physical and Chemical Transducers*, Jan. 25, 1999, vol. 54, No. 1-2, pp. 3-15.

Lakowicz, J.R. et al. Plasmon-controlled fluorescence: A new detection technology, *Proceedings of SPIE, International Society for Optical Engineering*, Jan. 1, 2006, vol. 6099, pp. 60909-1-3.

Vengurlekar, A. et al. Surface plasmon enhanced photon drag in metal films, *Applied Physics Letters, American Institute of Physics*, Aug. 26, 2005, vol. 87, No. 9, pp. 091118-1-091118-3.

\* cited by examiner

PLASMONIC ELECTRICITY

CROSS-REFERENCE TO RELATED APPLICATIONS

This application is a 35 U.S.C. §371 application of International Patent Application No. PCT/US2010/060174 filed on Dec. 14, 2010 which in turn claims priority to U.S. Provisional Patent Application No. 61/286,331 filed on Dec. 14, 2009, the content of which is hereby incorporated by reference herein for all purposes.

BACKGROUND OF THE INVENTION

Technical Field

The present invention is directed to systems that generate a current of electrical energy and additionally detection systems and methods that detect fluorescence, luminescence, chemiluminescence or phosphorescence signatures in the form of an electrical signal conducted by metallic structures.

Background of Related Art

The identification and quantification of proteins and other biomolecules using bioassays are of great importance in biomedical and biochemical applications.[1-3] Fluorescence is the dominant technology in most of these applications, where a biomolecule of interest is detected by fluorescence emission from its fluorophore labeled binding partner.[4,5] Fluorescence-based bioassays those carried out on planar surfaces generally lack sensitivity and require expensive optical instruments.[6,7] In addition, the biorecognition events in these assays are inherently slow (several minutes to hours).[6,7] The sensitivity of the fluorescence-based assays can be improved, without the use of high-end optical instruments, by incorporating plasmon resonant particles (PSPs) into these assays.[8,9] The improved sensitivity is made possible by the increase in fluorescence signatures and decreased lifetimes of fluorophores placed in close proximity to PSPs, described by a phenomenon called Metal-Enhanced Fluorescence (MEF).[8,10] In MEF-based bioassays, PSPs (generally silver nanoparticles) are deposited onto the planar surface and the bioassay is constructed on the PSPs.[8] Since the size of most biomolecules are smaller than PSPs (20-100 nm), fluorophores are positioned within a distance where their emission is increased due to their interactions with the surface plasmons of PSPs.[10]

The interactions of luminescent species with the close-proximity metallic nanoparticles have been extensively studied. These near-field interactions, are for the most part very complex, but can simply be understood phenomenologically as due to a close-proximity fluorophore inducing a mirror dipole in the metal, which in turn radiates the coupled quanta, in the form of emission, FIG. 1A. This interaction has been appropriately previously called "Metal-Enhanced Fluorescence".

For decades fluorescence-based technologies have relied on photo detectors to convert photon fluxes into digital signatures such as photomultiplier tube or charge coupled device (CCD) camera. Nearly all such instruments encompass one or more of these types of detectors. However, such detectors are expensive and require an additional piece of equipment. Thus it would be advantageous to detect fluorescence, luminescence, chemiluminescence, bioluminescence or phosphorescence signatures in the form of an electrical signal conducted by metallic structures.

SUMMARY OF THE INVENTION

The present invention relates to detection systems and methods that detect emission signals such as fluorescence, luminescence, chemiluminescence or phosphorescence signatures in the form of an electrical signal conducted by metallic structures caused by the transfer of energy from the fluorescence, luminescence, chemiluminescence or phosphorescence emitting probes to surface of the metallic particles. Thus, the present invention provides for detecting fluorescence digitally and directly without the need for expensive detectors.

Generally a traditional fluorophore may be used as an excitable molecule source that emits energy to induce a mirror dipole moment in the metallic surface. Further, inducing excitable probes or label sources that will produce plasmonic electricity when the probes or labels are in the near field, i.e. close-to the metal structures may include but are not limited to, Quantum Dots (Qdots); Chemiluminescence Alkaline Phosphatase and other chemiluminescence labels; Fluorospheres, i.e. fluospheres and Transfluospheres; Polymer beads doped with one or more fluorescent labels; Fluorescent Microspheres; Silicon nanoparticles; Silica and silicate doped materials; Semi conductor materials; E-type fluorescent luminophores; P-type fluorescent luminophores; Fluo-3 and Fluo-4 Calcium indicators; Calcium Green indicator; Fluozin Zinc indicators; Phen Green for the detection of a broad range of ions including $Cu^{2+}$, $Cu^+$ etc; Newport Green for the detection of $Zn^{2+}$; Leadmium Green dye for the measurement of lead and cadmium; Magnesium green for the electric detection of free magnesium; Mag-fura-2 and Mag-indo-1 for magnesium detection; Mag-fluo-4 for both calcium and magnesium detection in both free solution and intercellular; Phycobiliproteins (many different forms); Bucky balls, $C_{60}$ etc; Carbon nanotubes; Cardio green/indocyanine green fluorescent indicators; Metallic colloids of Ag, Au, Pt, Fe Pd, Cu, Zn, Rh, Cr, Pb etc and mixed colloidal metal combinations; pH indicators such as SNARF-1, SNARF-4F, SNARF-5F, Dextran BCECF etc; 6-chloro-9-nitro-5-oxo-5H-benzo{a}phenoxazine (CNOB) for the detection of nitroreductase and nitrate reductase activity; SYTOX dead cell stains, such as SYTOX Blue, green, Orange, Red; DAPI and the Propidium Iodide labels; Probes for double stranded DNA detection such as Ethidium bromide, Picogreen and Syber green; Alexa fluorophore range of dyes; BODIPY and related structural dyes; Cellular and Organelle lights (genetically encoded proteins); Green Fluorescent Protein (GFP) and its analogues; Coumarin dyes; Prodan and related structural dyes; Voltage sensitive probes such as $DisBAC_4(3)$ and CC2-DMPE; and/or Ncode miRNA labeling fluorophores In one aspect the present invention relates to a system for generating electrical current, the system comprising:
  i. a substrate comprising spatially separated metallic structures positioned on the substrate, wherein the metallic material is shaped as particles, nanostructures, island or colloids and at least partially covered with a polar solution;
  ii. a set of electrically conductive electrodes communicatively contacting at least two of the metallic structures positioned thereon;
  iii. an excitable probe that emits fluorescence, luminescence, or phosphorescence signatures when excited by electromagnetic energy and such excitation induces a mirror dipole in the metallic structures that are positioned from about 5 nm to about 50 nm from the excitable probe thereby causing plasmonic current flow.

Importantly the current is increased as the amount of excitable probes increases, thereby providing for an assay that provides an electrical signal proportional to the amount of binding of excitable probes to target substances.

The method and system described above may be used in multiple detecting systems, including but not limited to, immunoassays, hybridization assays, resonance energy transfer assays, polarization/anisotropy based assays, chemiluminescence based assays, luminescence based assays, enzyme-linked immunosorbent assays.

In another aspect, the present invention provides for a detection system comprising:
- a. conductive metallic structures positioned on a surface, wherein the metallic structures are shaped as particles, nanostructures, islands or colloids;
- b. at least one fluorophore for disposing near the conductive metallic structures, wherein the fluorophore is capable of inducing a mirror dipole in the metallic structures, wherein the fluorophore is positioned from about 5 nm to about 50 nm from the conduction metallic structures;
- c. a first and second electrode communicatively connected to at least two of the conductive metallic structures; wherein the first and second electrodes are communicatively connected to a current reading device;
- d. an electromagnetic energy source to excite the fluorophore and to induce a mirror dipole in the metallic material causing plasmonic current flow, wherein electromagnetic energy source is positioned a distance from the first or second electrode to increase current to be detected by the current reading device.

The present invention includes fluorescence, luminescence, chemiluminescence or phosphorescence components that have the ability to emit light energy when contacted with radiation in the range from UV to IR.

In another aspect the present invention relates to a method of metal-enhanced fluorescence sensing, comprising:
- a. applying conductive metallic structures to a surface used in a detection system, wherein the surface includes glass, cellulose, quartz, or a polymeric material, wherein the surface has a first and second end, wherein the first and second end and at least some of the metallic structures are communicatively connected to a first and second electrodes, wherein the electrodes have a current measuring device positioned therebetween;
- b. providing a polar solution for covering the conductive metallic structures;
- c. introducing at least one excitable probe for disposing near the conductive metallic surface, wherein the excitable probe is capable of excitation causing a dipole moment and/or fluorescing;
- d. exciting the excitable probe with an electromagnetic source to cause the dipole moment and/or fluorescing and whereby such excitement induces a dipole in the metallic material causing plasmonic current flow;
- e. measuring the plasmonic current flow with the current reading device, such as ampmeter.

Preferably, the electrodes are separated by a sufficient distance to provide optimal current readings, wherein the separation is from about from about 5 nm to 100 nm.

In yet another aspect, the present invention provides a method for detecting a targeted pathogen in a sample without the use of a photodetector, the method comprising:
- a. providing a system comprising:
  - i. immobilized metallic structures positioned on a surface substrate in a polar solution, wherein the substrate has a first and second end and wherein the first and second end of the substrate include electrodes or at least some metallic structures are communicatively connected to a first and second electrode, wherein the immobilized metallic structures have attached thereto an immobilized capture DNA sequence probe complementary to a known DNA sequence of the target pathogen; and
  - ii. a free capture DNA sequence probe complementary to a known DNA sequence of the target pathogen, wherein the free capture DNA sequence probe has attached thereto a fluorophore or equivalent thereof;
- b. contacting the sample with the immobilized capture DNA sequence probe, wherein any DNA sequence of the target pathogen binds to the immobilized capture DNA sequence probe;
- c. contacting the bound DNA sequence of the target pathogen with the free capture DNA sequence probe, wherein binding of the free capture DNA sequence probe to the DNA sequence of the target pathogen causes the fluorophore or equivalent thereof to be positioned from about 5 nm to about 50 nm from the immobilized metallic structures to induce a dipole in the metallic material;
- d. irradiating the system with electromagnetic energy in a range from UV to IR to excite the fluorophore or equivalent thereof positioned a predetermined distance from the metallic material; and
- e. measuring the plasmonic current flow with a current flow detector positioned between the electrodes, wherein the current is proportional to the amount of fluorophore or equivalent thereof.

Preferably, the conductive metallic material takes the form of metallic particles, such as, nanostructures, islands, colloids, porous matrix or a semi-continuous metallic surface. The metallic element may include any form of metals such as silver, gold, platinum, zinc, aluminum, indium, palladium, rhodium iron, nickel, copper, and combination thereof and more preferably the metallic material is silver. The substrate can include, glass, quartz, cellulose and/or a polymeric material.

Preferably, the metallic material is in the form of particles and separated a distance to provide optimal current flow and wherein resistance is higher than that of a continuous metal film. Preferably, at least a portion of each metallic particle is in contact with a polar solvent or a dipolar aprotic solvent that has a dipole moment and inducible, such as water, other polar solvents, including methanol or acetic acid, ionic salt solutions and/or acetone, ethylene acetate.

The molecule that is capable of fluorescing and/or upon excitation by electromagnetic energy exhibits a dipole moment includes, but is not limited to fluorophores, chromophores, lumophores, biomolecules or any molecule or device that provides for intrinsic or extrinsic luminescence activity.

In one aspect, the present invention relates to bioassay systems comprising metallic surfaces for the enhancement of effects of chemiluminescence based reactions positioned near the metallic surfaces, wherein metallic surface plasmons are excited by a chemically induced electronically excited state of a chemiluminescent species and transference of energy from the chemiluminescence reaction induces plasmonic current flow in the metallic structures that can be measured with a current flow device.

In a still further aspect, the present invention relates to an assay, the method comprising:
- a. providing at least one vessel or container; wherein a first and second electrode are positioned within the vessel or communicatively connected thereto;

b. introducing metallic nanostructures into the vessel, wherein the vessel includes a polar solution, wherein the metallic nanostructures can be free in solution or connected to a surface of the vessel and communicatively connected to the first and second electrodes;

c. introducing a molecule that exhibits dipole activity upon excitation and disposing such molecule near the metallic nanostructures, wherein the molecule is positioned a predetermined proximity to the metallic nanostructures to induce a mirror dipole in the metallic nanostructures; and d. measuring the current flow.

In yet another aspect, the present invention relates to a method of metal-enhanced chemiluminescence sensing, comprising:

a. applying metallic structures that are spatially separated to a surface used in a detection system, wherein at two metallic structures are connected to a set of electrodes;

b. introducing a solution containing at least one biomolecule for disposing near the metallic structures, wherein the biomolecule comprises a chemiluminescent label;

c. triggering the chemiluminescent label to induce a chemically electronically excited state at a distance from about 5 nm to about 30 nm from the metallic structures thereby generating metallic surface plasmons and inducing a mirror dipole in the metallic structures and generating a current flow in the solution.

In another aspect, the present invention relates to a system for measuring chemiluminescence, the system comprising:

i. a partially metalized surface positioned on a surface substrate, wherein the metalized surface is in contact with a polar solvent wherein the substrate or partially metalized is connected to a set of electrodes;

ii. a connector molecule attached to the partially metallized surface or near the partially metallized surface for binding or capture of a desired molecule in a testing sample;

iii. a detector molecule having an affinity for the desired molecule, wherein the detector molecule comprises a chemiluminescence label;

iv. a triggering component that chemically reacts with the chemiluminescence label to generate a chemically induced electronically exited state and induce a mirror dipole in the partially metallic surface and inducing a current flow in the polar solvent, wherein the current flow is measured and such flow is proportional to the amount of desired molecule in the testing sample.

A system for conducting current, the system comprising:

a. metallic particles dispersed in a polar solution, wherein the metallic particles are adaptable for connecting to an intrinsic or extrinsic fluorophore molecule and wherein the metallic particles are positioned from about 5 nm to about 20 nm from the metallic particles; and b. a source of electromagnetic energy to deliver radiation in a range of UV to IR and in an amount sufficient to excite the fluorophore or label source, wherein such excitation causes a mirror dipole in the metallic particles and induces current flow in the solution.

Still further, the present invention relates to using the present concept of plasmonic electricity in combination with a microscope that can provide visual images and a direct digital readout of induced plasmonic current flow, wherein the system includes a substrate having metallic particle deposited thereon, wherein the substrate is a slide adapted for use in a microscope and the substrate or two of the metallic particles are adapted with electrodes and attached to a current reading device.

Other aspects and advantages of the invention will be more fully apparent from the ensuing disclosure and appended claims.

DETAILED DESCRIPTION OF THE INVENTION

The present invention relates to systems and methods for generating a current flow by positioning a fluorophore near a metallic particle and wherein excitation of the fluorophore causes an induced mirror dipole in the metallic particle and a flow of electrical current from one metallic particle to an adjacent metallic particle in communicative contact in a polar solvent.

The present invention describes the detection of fluorescence (luminescence, chemiluminescence, phosphorescence) signatures in the form of electrical signals in thin metallic films. Normally, fluorescence or luminescence emission is detected with a detector, PMT (Photomultiplier tube) or CCD (charge coupled device) camera etc. However, fluorophores in close proximity to the metal can induce currents in the metal, which can be detected using an ammeter as shown in FIG. 1 B.

Figure 2:
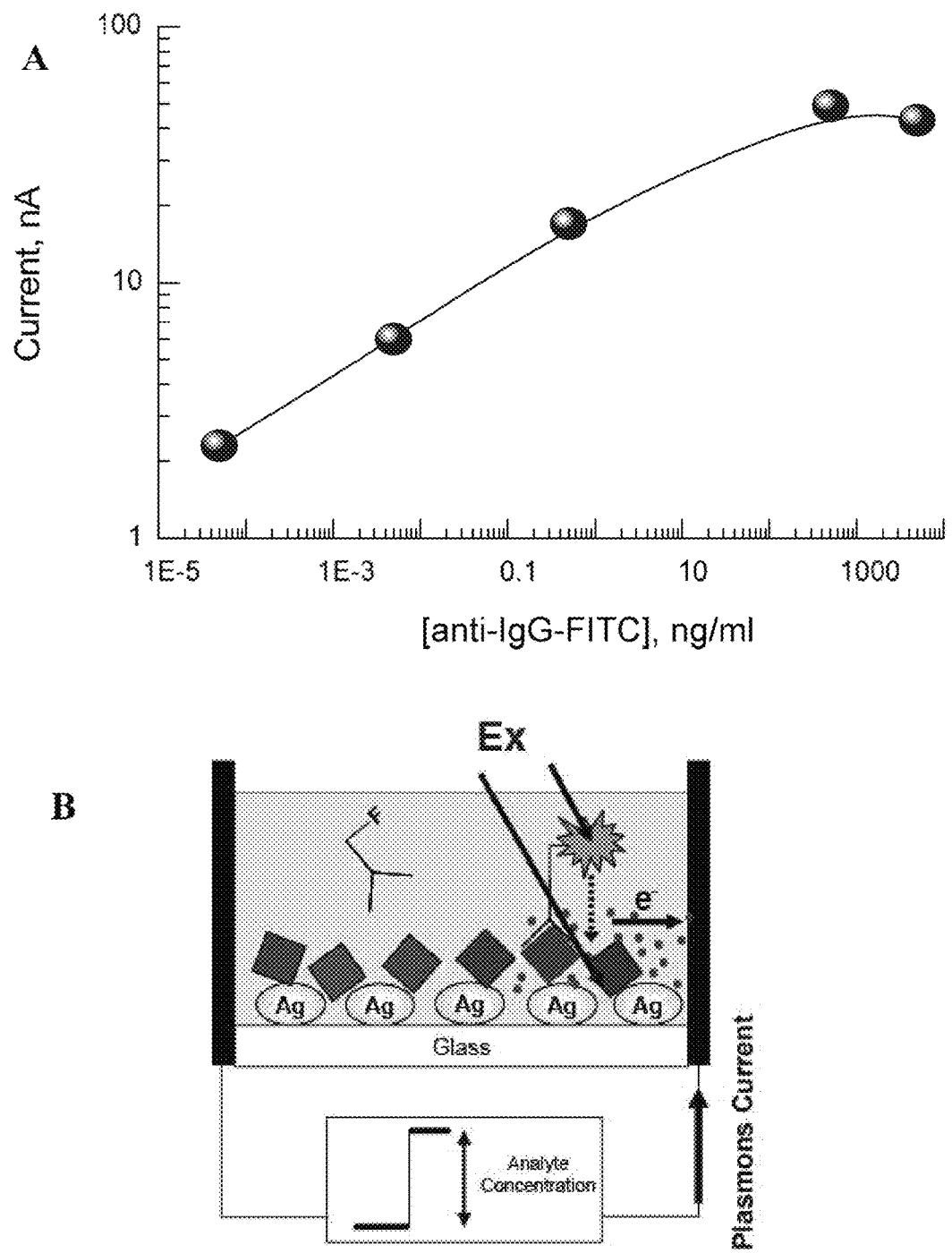
FIG. 2 shows dependence of the plasmonic current (PC) in the SiF covered by rabbit IgG upon the concentration of added anti-IgG, labeled with fluorescein with graphical interpretation of the experiment.

The notion of direct detection of fluorescence is an enormous breakthrough in fluorescence spectroscopy and its applications. Potential uses for this technology include immunoassays, textiles and fabrics that provide metallic containing structures that can be used to powers hand held devices wherein the antigen concentration can now be read directly and most importantly digitally, as shown in FIG. 2, without the need for an external detector. Another application is in solar energy conversion, where daylight excited fluorophores can generate electrical currents in thin metallic films.

"Excitable molecule," as used herein, means any substance that can be excited by electromagnetic energy and induce a mirror dipole metallic surface in close proximity to the metallic structures. Excitably molecule is intended to encompass a chemical or biochemical molecule or fragments thereof that is capable of interacting or reacting specifically with an analyte of interest in a sample to provide one or more optical signals.

Excitably molecule within its meaning can include but not limited to, Fluorophores, Quantum Dots (Qdots); Chemiluminescence Alkaline Phosphatase and other chemiluminescence labels; Fluorospheres, i.e. fluospheres and Transfluospheres; Polymer beads doped with one or more fluorescent labels; Fluorescent Microspheres; Silicon nanoparticles; Silica and silicate doped materials; Semi conductor materials; E-type fluorescent luminophores; P-type fluorescent luminophores; Fluo-3 and Fluo-4 Calcium indicators; Calcium Green indicator; Fluozin Zinc indicators; Phen Green for the detection of a broad range of ions including $Cu^{2+}$, $Cu^+$ etc; Newport Green for the detection of $Zn^{2+}$; Leadmium Green dye for the measurement of lead and cadmium; Magnesium green for the electric detection of free magnesium; Mag-fura-2 and Mag-indo-1 for magnesium detection; Mag-fluo-4 for both calcium and magnesium detection in both free solution and intercellular; Phycobiliproteins (many different forms); Bucky balls, $C_{60}$ etc; Carbon nanotubes; Cardio green/indocyanine green fluorescent indicators; Metallic colloids of Ag, Au, Pt, Fe Pd, Cu, Zn, Rh, Cr, Pb etc and mixed colloidal metal combinations; pH indicators such as SNARF-1, SNARF-4F, SNARF-5F, Dextran BCECF etc; 6-chloro-9-nitro-5-oxo-5H-benzo{a}phenoxazine (CNOB) for the detection of nitroreductase and nitrate reductase activity; SYTOX dead cell stains, such as SYTOX Blue, green, Orange, Red; DAPI and the Propidium Iodide labels; Probes for double stranded DNA detection such as Ethidium bromide, Picogreen and Syber green; Alexa fluorophore range of dyes; BODIPY and related structural dyes; Cellular and Organelle lights (genetically encoded proteins); Green Fluorescent Protein (GFP) and its analogues; Coumarin dyes; Prodan and related structural dyes; Voltage sensitive probes such as $DisBAC_4(3)$ and CC2-DMPE; and/or Ncode miRNA labeling fluorophores Fluorophores may includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3-diazol-4-yl chloride (NBD-Cl), ethidium bromide, Lucifer Yellow, 5-carboxyrhodamine 6G hydrochloride, Lissamine rhodamine B sulfonyl chloride, Texas Red™. sulfonyl chloride, BODIPY™, naphthalamine sulfonic acids including but not limited to 1-anilinonaphthalene-8-sulfonic acid (ANS) and 6-(p-toluidinyl) naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2 [(di-n-butylamino)-6 naphthyl]vinyl]pyridinium betaine (Naphtyl Styryl), 3,3' dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1, 4', 6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, green fluorescent proteins and metal-ligand complexes.

Representative intrinsic fluorophores include but are not limited to organic compounds having aromatic ring structures including but not limited to NADH, FAD, tyrosine, tryptophan, purines, pyrirmidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Embodiments of the present invention are applicable to chemiluminescence labels or moieties which participate in light-producing reactions in the presence of a triggering agent or cofactor. In the present application, for purposes of example and without limitation, a preferred embodiment will be discussed in terms of chemiluminescence labels and triggering agent. The label affixed to the detector molecule will be referred to as the "label" or "label agent". For purposes herein, "triggering agent or cofactor" is broadly used to describe any chemical species, other than the chemiluminescence labels which participate in a reaction and which produces a detectable response. Chemiluminescence labels and triggering agents produce a light response.

Examples of suitable chemiluminescence labels include but without limitation, peroxidase, bacterial luciferase, firefly luciferase, functionalized iron-porphyrin derivatives, luminal, isoluminol, acridinium esters, sulfonamide and others. A preferred chemiluminescent label includes xanthine oxidase with hypoxanthine as substrate. The triggering agent contains perborate, a Fe-EDTA complex and luminol. Choice of the particular chemiluminescence labels depends upon several factors which include the cost of preparing labeled members, the method to be used for covalent coupling to the detector molecule, and the size of the detector molecules and/or chemiluminescence label. Correspondingly, the choice of chemiluminescence triggering agent will depend upon the particular chemiluminescence label being used.

Chemiluminescent reactions have been intensely studied and are well documented in the literature. For example, peroxidase is well suited for attachment to the detector molecule for use as a chemiluminescence. The triggering agent effective for inducing light emission in the first reaction would then comprise hydrogen peroxide and luminol. Other triggering agents which could also be used to induce a light response in the presence of peroxidase include isobutyraldehyde and oxygen.

Procedures for labeling detector molecules, such as antibodies or antigens with peroxidase are known in the art. For example, to prepare peroxidase-labeled antibodies or antigens, peroxidase and antigens or antibodies are each reacted with N-succinimidyl 3-(2-pyridyldithio) proprionate (hereinafter SPDP) separately. SPDP-labeled peroxidase, or SPDP-labeled antigen or antibody is then reacted with dithiothreitol to produce thiol-labeled peroxidase, or thiol-labeled antigen or antibody. The thiol derivative is then allowed to couple with the SPDP-labeled antigen or antibody, or SPDP-labeled peroxidase.

Techniques for attaching antibodies or antigens to solid substrates are also well known in the art. For example, antibodies may be coupled covalently using glutaraldehyde to a silane derivative of borosilicate glass.

The term "biomolecule" means any molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Preferably, the biomolecule has a dipole moment when excited and thus can induce a mirror dipole in a metallic material in close proximity. Exemplary biomolecules include nucleic acids, aromatic carbon ring structures, NADH, FAD, amino acids, carbohydrates, steroids, flavins, proteins, DNA, RNA, oligonucleotides, peptide, nucleic acids, fatty acids, myoglobin, sugar groups such as glucose etc., vitamins, cofactors, purines, pyrimidines, formycin, lipids, phytochrome, phytofluor, peptides, lipids, antibodies, bilirubin, tryptaphan and phycobiliproptein.

There are many important assays that can directly benefit from immediate readouts and quicker kinetics. For example, myoglobin concentrations for heart attack patients, patients of toxic shock and pancreatitis. Thus, the present invention may optionally include the use of microwave energy or sonic energy to increase any reaction rates in an assay detection system. As such, the present invention can be used for points-of-care clinical assessment in emergency rooms.

The present invention may optionally include the use of microwave energy or sonic energy to increase any reaction rates in an assay detection system The assay systems of the present invention may further comprise a light or laser source for directing an energy beam on any included fluorophore to provide excitation energy. The laser beam may be positioned adjacent to the system for directing the beam at the molecular components. The laser may be any device capable of focusing an energy beam at a particular point on the solid or liquid source material for excitation and the laser may transmit RF, infrared, microwave to UV energy.

Any source, known to one skilled in the art may be used, such as a laser that emits light, wherein light is used in its broad sense, meaning electromagnetic radiation which propagates through space and includes not only visible light, but also infrared and ultraviolet radiation. Thus, a single instrument placed above the surface of the assay can be used to generate the energy to excite fluorescing molecules. The light can be emitted from a fiber continuously or intermittently, as desired.

Further, 2-photon excitation may be used at approximately 375 to 900 nm using continuous or short pulse width (<50 ps), high repetition rate (>1 MHz), laser diode sources. A variety of pulsed laser diode sources that will be compatible with fluorophores can be used with the present invention and are commercially available.

Still further, the present invention can be used with tunable Ti:Sapphire laser excitation and multiphoton microscopy.

The present invention provides for metallized islands of elliptical, spherical, triangular or rod-like forms. In exemplary cases, the elliptical islands have aspect ratios of 3/2, and the spherical colloids have diameters of 20-60 nm. However, the invention is not limited to any particular geometry. Using known coating techniques, the placement of metallic islands could be controlled precisely, as close as 10 to 50 nm apart.

The metallic material may be in the form of a porous three dimensional matrix. The three dimensional matrix may be a nano-porous three dimensional matrix. The metallic material may include metal colloid particles and/or metal-silica composite particles. The metallic material may comprise agglomerated metal particles and/or binary linked particles or metal particles in a polymer matrix. The three dimensional matrix may be formed from controlled pore glasses or using matrices assembled from the aggregation of silver-silica composites themselves. The matrices may be metallic nanoporous matrix, through which species will flow and be both detected and counted more efficiently.

The emission induction of a mirror dipole from the excited molecule to the metallic structure may be observed at distances according to the type of excitable molecule to be detected and the type of metal. For example, induction of a current may be observed when a fluorophore is positioned from about 5 nm to about 200 nm to metal surfaces. Preferable distances are about 5 nm to about 50 nm, and more preferably, 10 nm to about 30 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Different surface enhanced fluorescence effects are expected for mirrors, sub-wavelength or semi-transparent metal surfaces, silver island films or metal colloids. More dramatic effects are typically observed for islands and colloids as compared to continuous metallic surfaces. The silver islands had the remarkable effect of increasing the intensity 5-fold while decreasing the lifetime 100-fold. Such an effect can only be explained by an increase in the radiative decay rate.

Preparation of Silver Metal Islands

The island particles are prepared in clean beakers by reduction of metal ions using various reducing agents. For example, sodium hydroxide is added to a rapidly stirred silver nitrate solution forming a brown precipitate. Ammonium hydroxide is added to re-dissolve the precipitate. The solution is cooled and dried quartz slides are added to the beaker, followed by glucose. After stirring for 2 minutes, the mixture is warmed to 30° C. After 10-15 minutes, the mixture turns yellow-green and becomes cloudy. A thin film of silver particles has formed on the slides as can be seen from their brown green color. The slides are rinsed with pure water prior to use.

Alternative procedures for preparing metal particles are also available. Silver is primarily used because of the familiar color from the longer surface plasmon absorption of silver.

Preparation of Silver Colloids

Colloids can be prepared as suspensions by citrate reduction metals. Preferred metals are silver and gold. Again, gold may be because of the absorption of gold at shorter wavelengths. However, gold colloids may be used with longer wavelength red and NIR fluorophores.

The size of the colloids and their homogeneity can be determined by the extensive publications on the optical properties of metal particles available and the effects of interface chemistry on the optical property of colloids.

Metal particles can be bound to a surface by placing functional chemical groups such as cyanide (CN), amine ($NH_2$) or thiol (SH), on a glass or polymer substrate. Metal colloids are known to spontaneously bind to such surfaces with high affinity.[90, 91, 92]

Metallic colloids (or various other non-spherical shapes/particles) may also be incorporated into organic polymers, covalently or non-covalently, to form polymeric matrices, wherein the distance from diffusing species affords an increase in radiative decay rate and thus, an increase in quantum yield. Such polymeric matrices are ideal for sensing/flowing sensing applications of low concentration species.

The electrode system of the present invention may include a containment vessel that includes two electrodes, anode and cathode, attached to the vessel, communicatively connected to the metallic structures or the electrode can be inserted into solution. Generally the electrodes can be fabricated from any conductive metal and may include carbons, noble metals or alloys of Pt, Pd, Ir, Au, Ru, etc., noble metals or alloys deposited on a substrate such as Ti or Ta. Metals and metal alloys are preferred having a conductivity of greater than about $10^{-4}$ S/cm. In the alternative, wire electrodes can be directly attached to two of the metallic particles, wherein the metallic particles and attached wires are separated sufficiently to detect optimal current flow.

Further, the electrodes can be fabricated from any electrically conducting polymer, electrically conducting ceramic, electrically conducting glass, or combinations thereof including metal oxides and selected from tin, lead, vanadium, titanium, ruthenium, tantalum, rhodium, osmium, iridium, iron, cobalt, nickel, copper, molybdenum, niobium, chromium, manganese, lanthanum, or lanthanum series metals or alloys or combinations thereof, and possibly containing additives like calcium to increase electrical conductivity.

Electrolytes in an aqueous solution or polar solvents may include an ionically conductive aqueous or non-aqueous solution or material, which enhances the movement of current between electrodes. The electrolyte may include NaCl, KCl, $NH_4Cl$, NaI, KI, NaAc, NaOH, $AgNO_3$, $CuSO_4$, $LiClO_4$, $NaClO_4$, $KClO_4$, $AgClO_4$, $NaBrO_4$, etc. The polar solvents may include water, ethanol, and methanol.

This embodiment of the present invention may also have vast applications in clinical medicine, environmental monitoring applications, homeland security such as rapid detection of low concentration species with a direct and digital readout, industrial processes, pharmaceutical industries such as monitoring species, and sensors for use in reduced atmospheres such as biohazard clean rooms and space light.

Figure 1A:
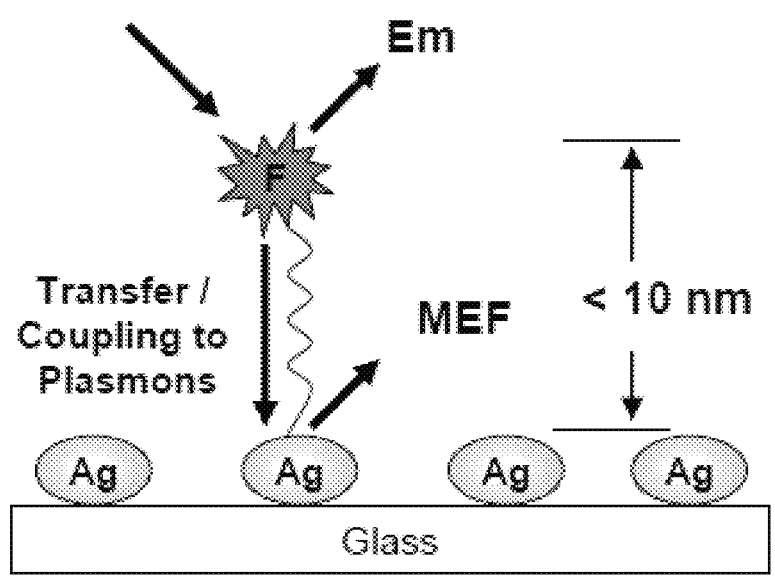
FIG. 1 shows graphical representation of the current interpretation of Metal-Enhanced Fluorescence (A), Plasmonic Current is due to coupling of excited fluorophore or label source to the surface plasmons of silver nanoparticles (B), a electrode setup with attached ammeter for measuring current, F—Fluorophore, MEF—Metal-Enhanced Fluorescence, PC—Plasmonic Current, Ag—Silver nanoparticles.
Figure 1B:
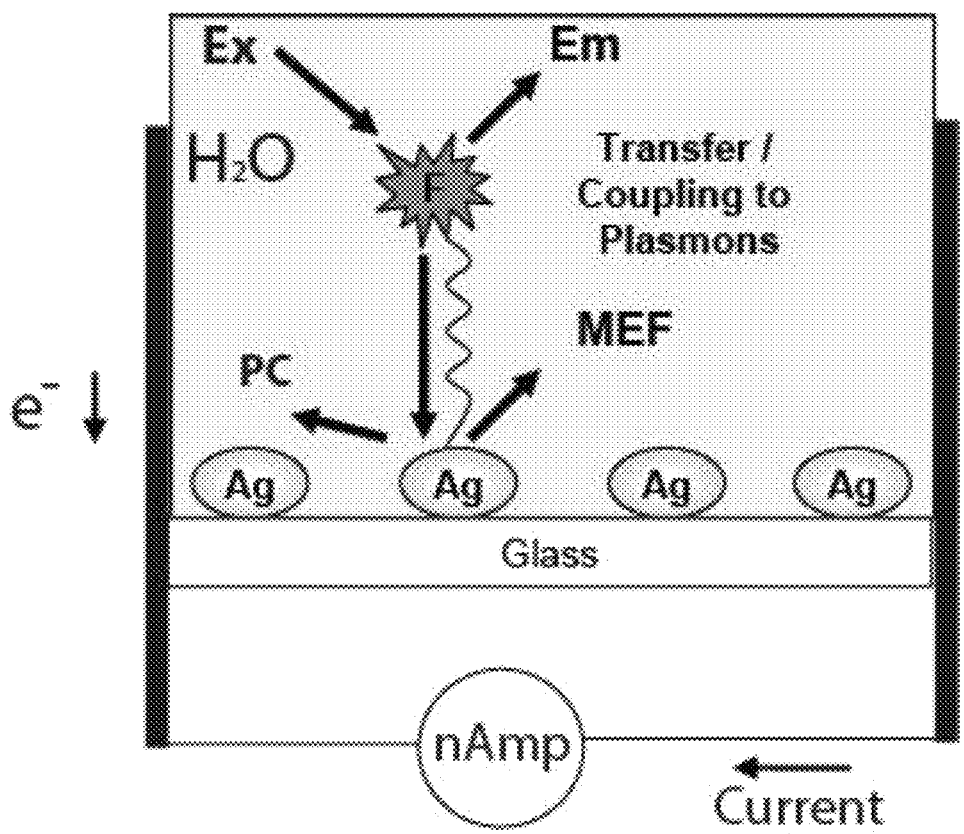
Figure 3A:
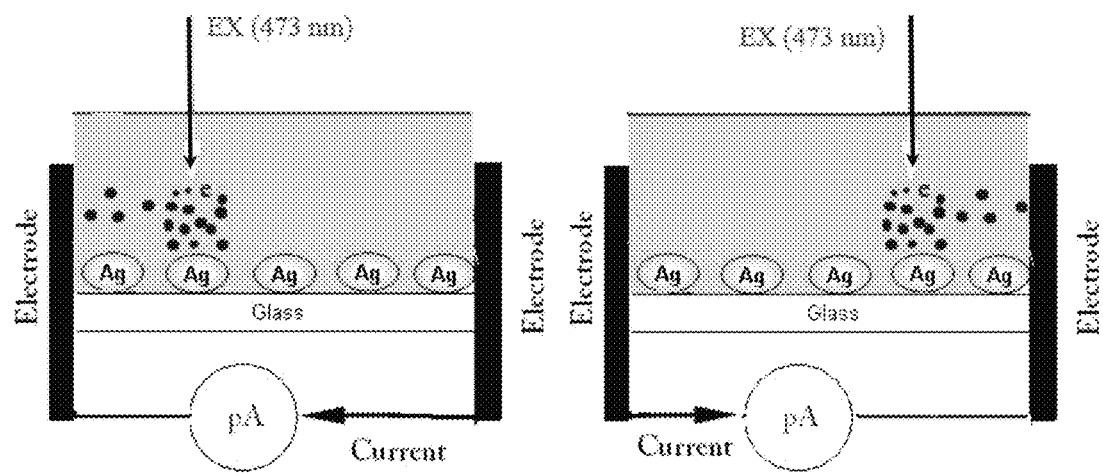
FIG. 3A shows plasmonic current (PC) induced by the laser (473 nm) in SiF (R>>200 MOhm/cm) covered by Fluorescein isothiocyanate (FITC) in water. The distance between electrodes is 10 mm. The excitation spot on SiF was moved from the left electrode to the right electrode.
Figure 3A:
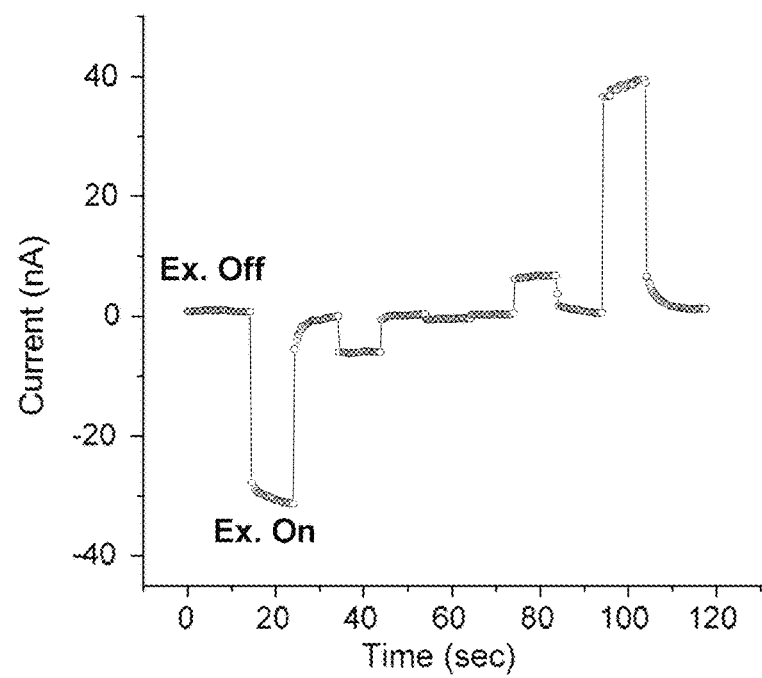
Figure 3B:
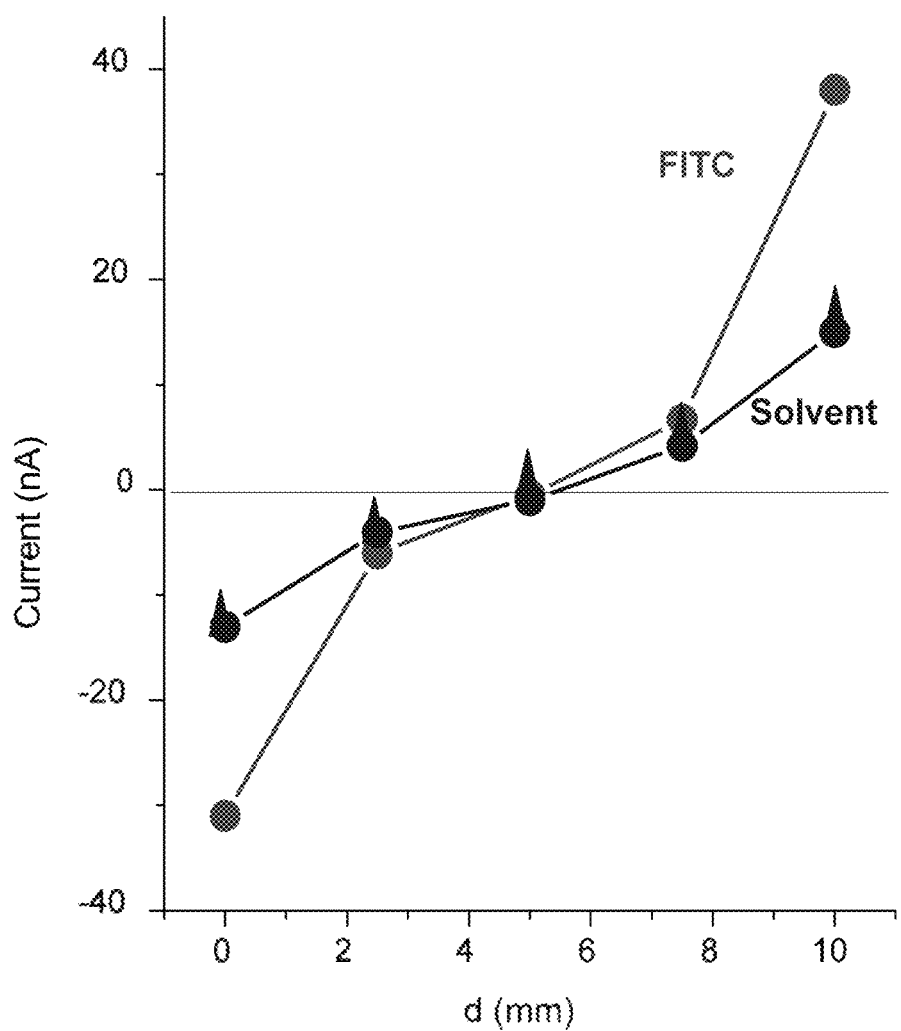
As shown in FIG. 3B, the direction of observed plasmonic current flow, non-linearly depends on the distance of the excitation spot from the electrodes themselves.

When a fluorophore induces a mirror dipole in a silver metallic structure, near-field photo-induced currents (photo currents) are formed. These small currents are able to migrate across the silvered metallic structures. Interestingly, the greater the concentration of fluorophore present, there is a corresponding increase in induced current. FIG. 3, shows the extent of photo-induced current on the concentration of fluorescein (a fluorescent probe) in water, placed between 2 electrodes on a silver island film. Remarkably, the current increases significantly over the 3 $log_{10}$ concentrations of fluorescent probe studied. This result suggests that the more fluorophore present close to metal, then the greater the induced current flow. It is interesting to note, that in Traditional Fluorescence-based immunoassays, the extent of detected fluorophore (usually fluorescence intensity) is directly related to the analyte concentration to be determined in the assay. The results shown herein suggest, that fluorescence-based immunoassays can be constructed on silvered surfaces, where the concentration of analyte (antigen) can be determined by the induced currents in the metal, as depicted by FIG. 1A and FIG. 2. Remarkably, the reading is purely digital and is a direct measure of the coupled fluorescence. In contrast, fluorescence based immunoassays in the world today, detect the fluorescence from the assay directly, then covert the signal which can be displayed digitally. Subsequently, the present approach is a significant breakthrough in how fluorescence is measured and quantified. FIG. 3A also demonstrates that the direction of current flow can be determined by the position of the excitation spot relative to the sampling electrode. The current is directly symmetrical, i.e. a positive or negative current, with regard to the position of the laser spot and the electrode.

Figure 4:
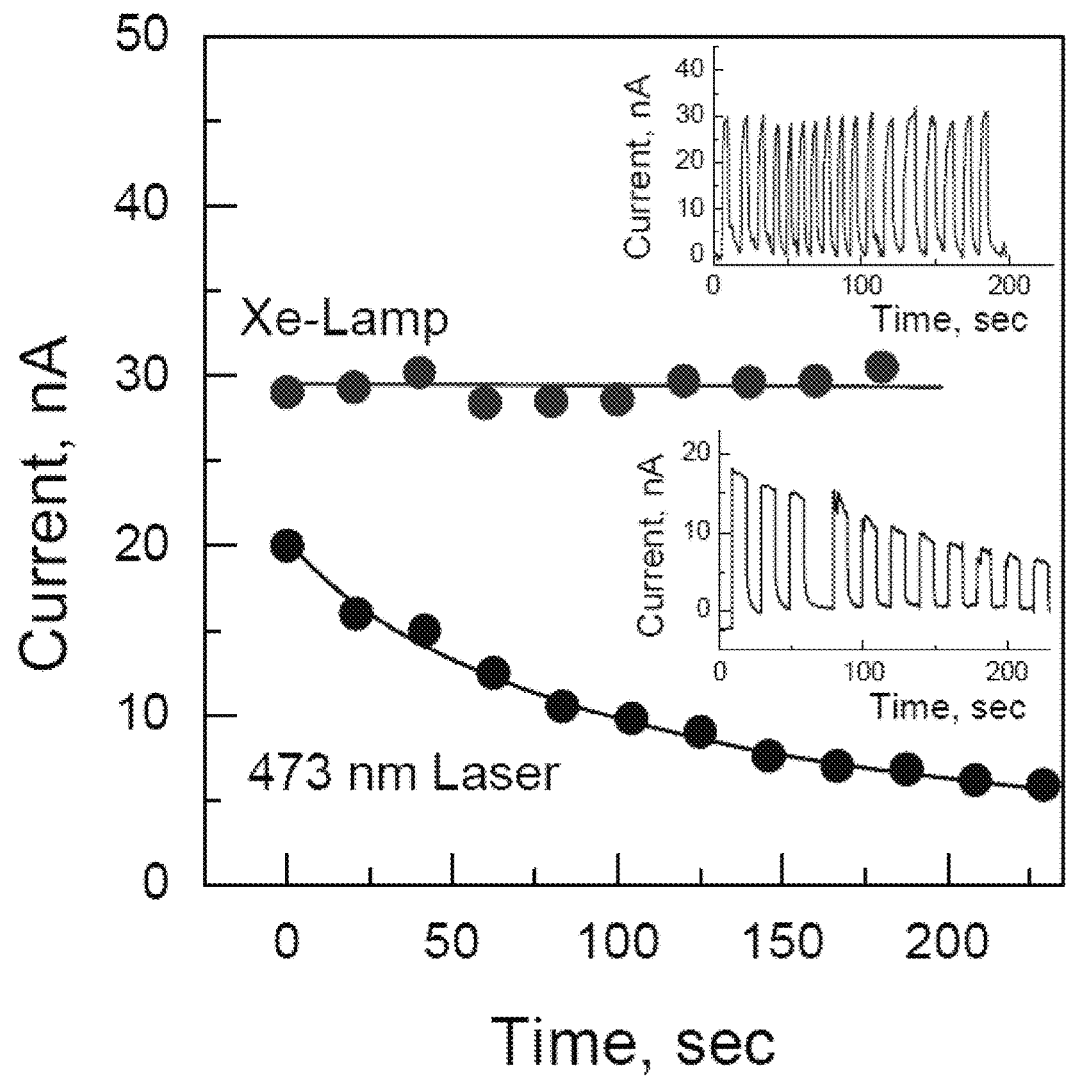
FIG. 4 shows irradiation of FITC-SiFs ($H_2O$) using a Xe-arc lamp and also a 473 nm laser.

Other Potential Uses of the Technology:

While direct measurement of fluorescence-based signatures is a big field (business) in itself, one very promising application of the technology is likely to be in solar energy conversion. It is also envisioned that fluorophore coated silver substrates can induce currents in metal films after sun light illumination, FIG. 4. In this figure, a Xenon arc lamp is used to simulate sun light. As can be seen in FIG. 4—top, insert, as the sun light is gated on and off, the current modulates, demonstrating that the effect is due to direct illumination of SiFs/fluorophores with light. Laser light also causes plasmonic current as shown in the bottom figure of FIG. 4.

Figure 5:
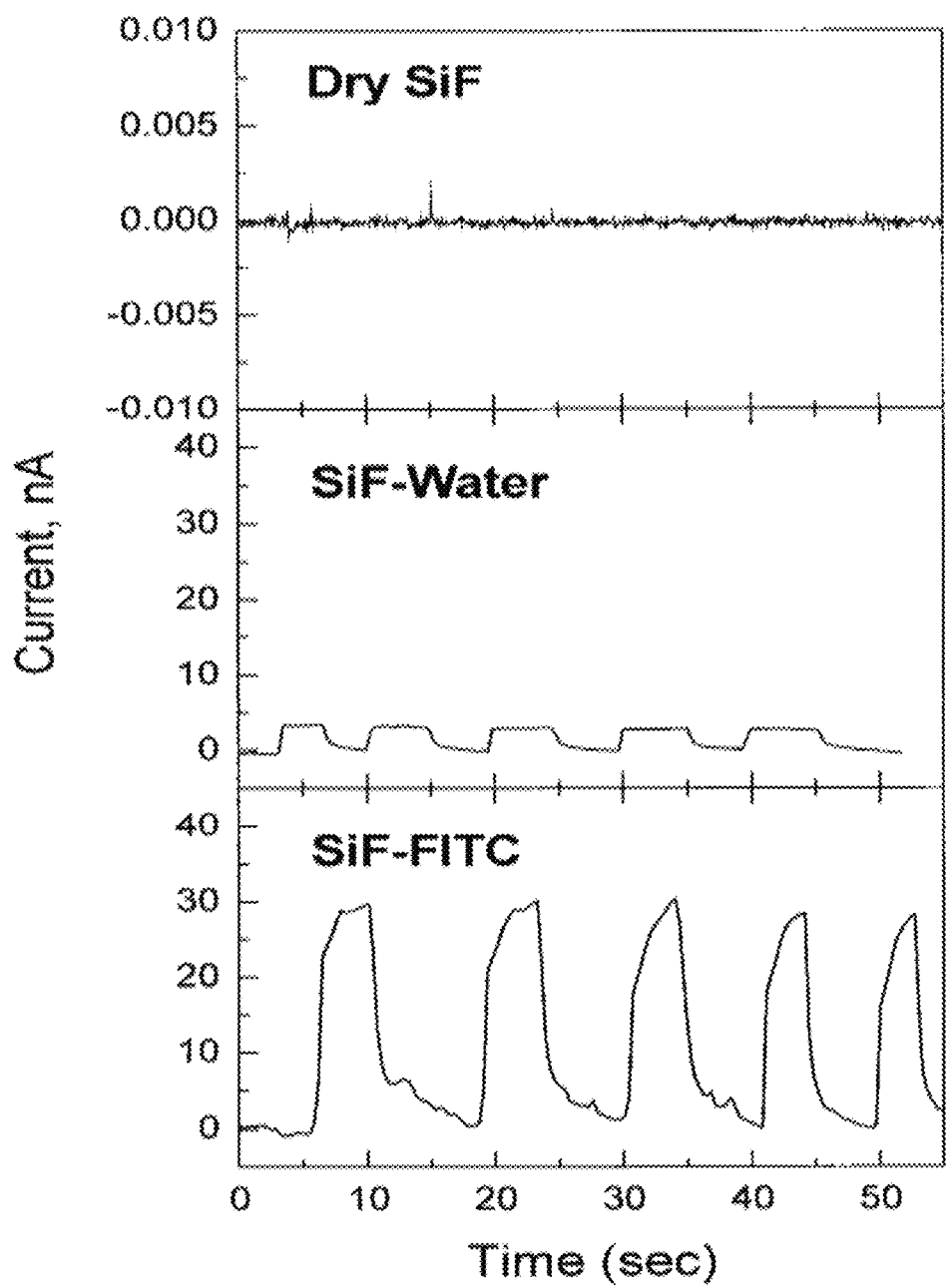
FIG. 5 shows Top: Current induced in SiFs (dry sample); Middle: Current induced by wet SiFs ($H_2O$); Bottom: SiFs coated with (FITC)-water solution. Irradiation of the slides was performed with a Xe-arc lamp. Manual light shut off was achieved sharply in about 5 sec intervals. SiF—Silver Island Films.
Figure 6A:
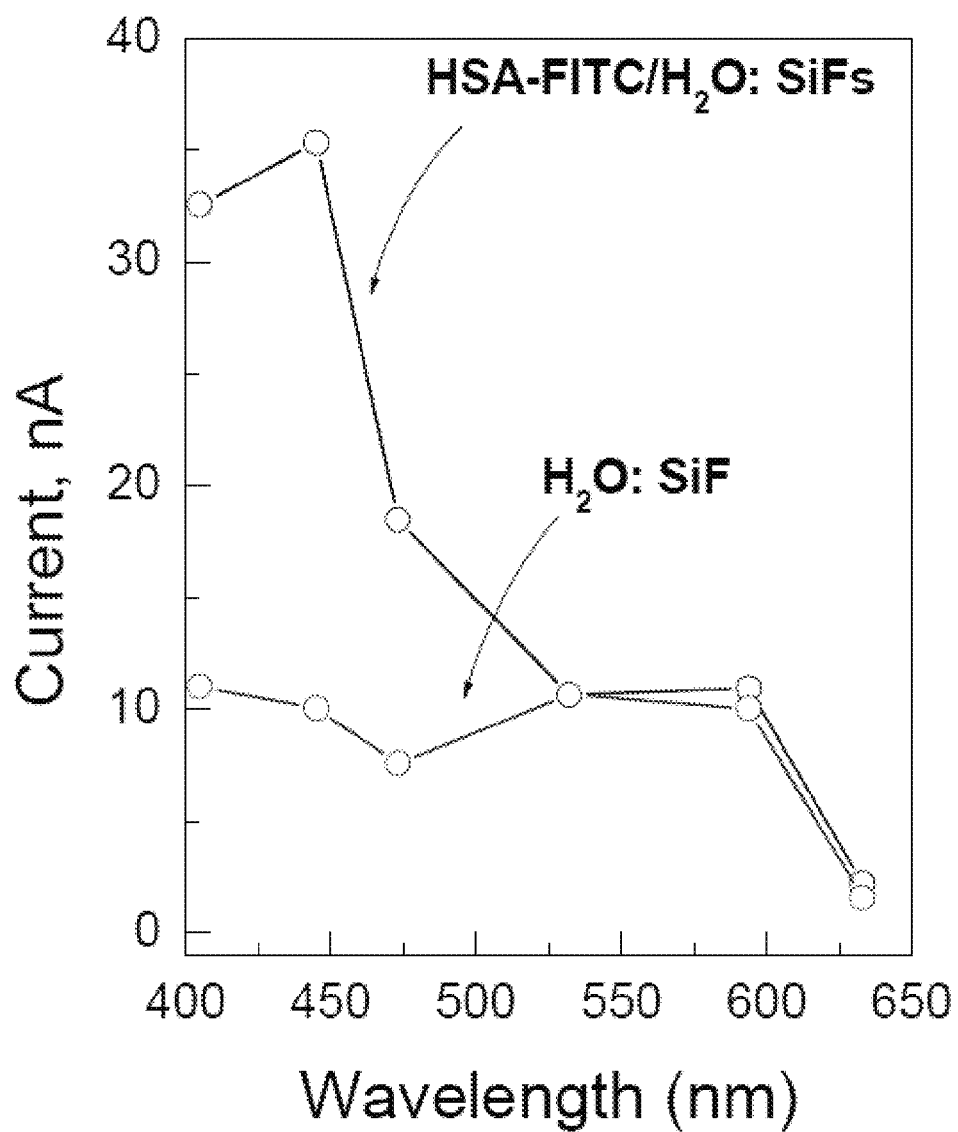
FIGS. 6A and B show the dependence of the current, induced by light in SiF containing deposited human serum albumin labeled by FITC (HSA-FITC) or solvent (water), upon wavelength of excitation. (a) observed current corrected on Laser power deviations; (b) Contribution of the HSA-FITC to the current, absorption of the SiF and FITC. Excitation was done by lasers. Power of light generation was adjusted by the neutral filters (NF) to about 20-50 mW. Correction of the current at certain wavelengths was done by normalizing to the power of 46.5 mW (power of 473 nm-Laser (500 mW) attenuated by N-filter (OD473=1.04 o.u.). [HSA-FITC]=0.65 mM in water, pH 5.5.
Figure 6B:
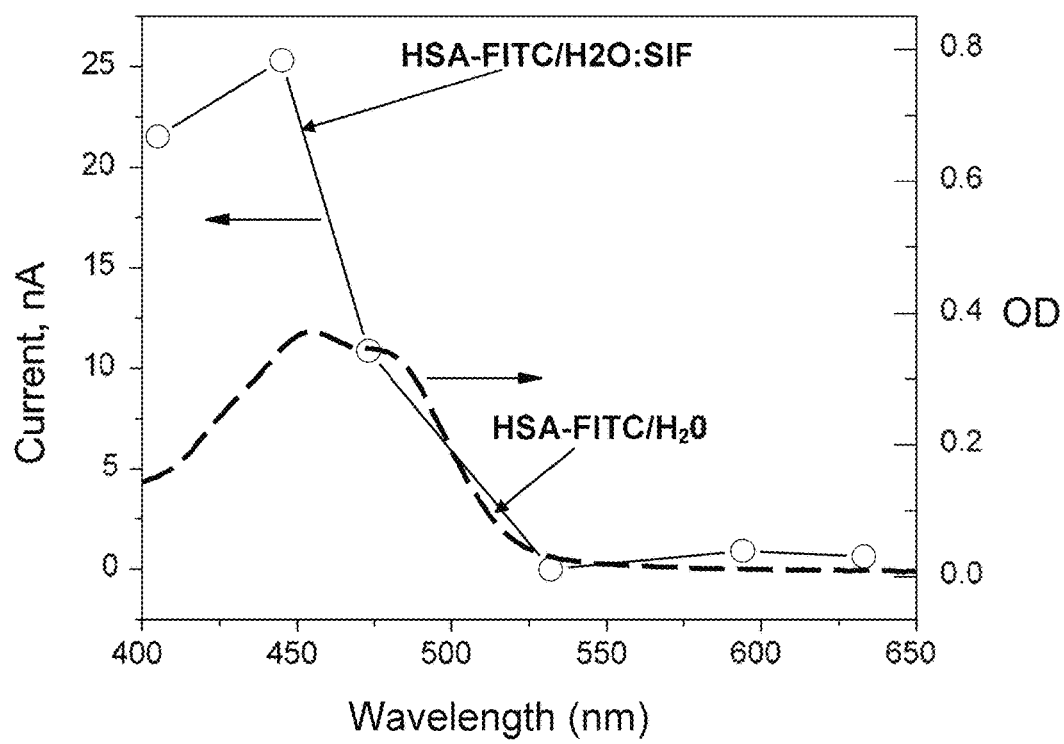

Demonstration of Plasmonic Current/Electricity:

FIG. 5—top shows that dry Sifs (Silver Island Films) have little to no current in them when illuminated by an external light source, a value of 0 nA determined. However, when an aqueous solution is placed on top of the SiFs a current of <5 nA is produced. Interestingly, the current modulates as the Xe-arc lamp light source is modulated on-off. This background current is due to the water dipole interaction with the metal SiFs. However, when a fluorophore (fluorescent, phosphorescent or chemiluminescent species) is added to the water solution on SiFs, a significant current is further observed, increasing to as much as 30 nA. This current is due to interaction of the fluorophore dipole with the metal, as graphically indicated in FIG. 1B. As can be seen from this figure, the presence of fluorophores close to Sifs (and indeed other metals) causes a current, which is directly proportional to the concentration of fluorophore, making it an excellent technology for the direct detection of Fluorescence. In addition and remarkably, the current generation in the metal is wavelength dependent and appears to follow both the absorption spectra of the Sifs and the emission spectra of the metal, as shown in FIGS. 6 A and B.

Figure 7:
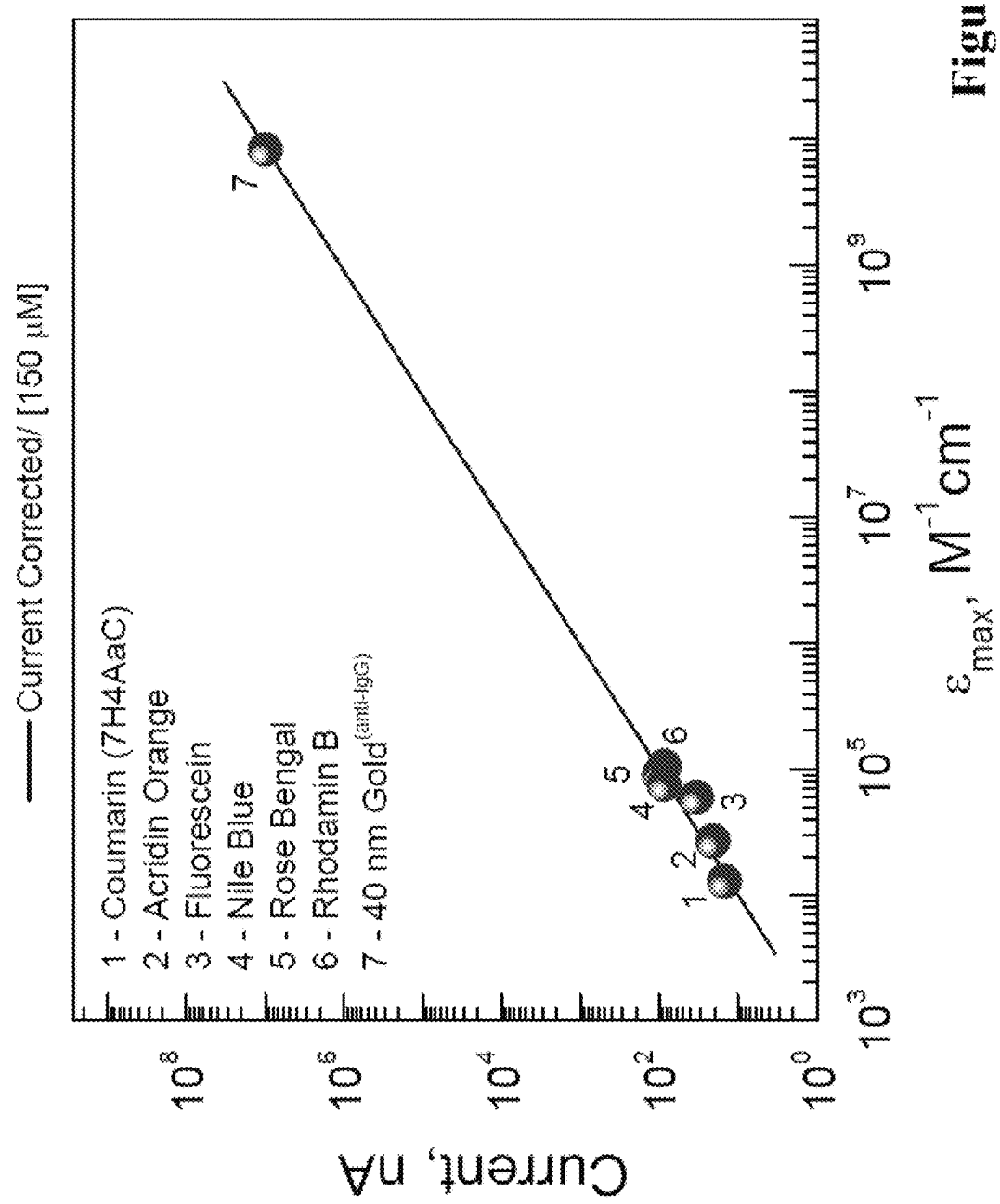
FIG. 7 shows the dependence of the current, generated by SiF-Dye system upon 473 nm laser irradiation, on extinction coefficient of the studied dyes. Observed current was normalized to the current induced by dyes at the Concentration of 150 mM, taking linear dependence of the current vs dye Concentration.

FIG. 7 shows that different types of chromophores and even gold and silver colloids can induce plasmonic current. For excitable molecules used as probes, the extent of plasmonic electricity is dependent on: concentration of probe/fluorophore in solution; extinction coefficient of fluorophore and oscillator strength of a particular transition. Figure In addition, the magnitude of the induced current is dependent on the molar extinction coefficient of the close-proximity dipole, FIG. 7, which implies that other plasmonics nanostructures will be excellent for inducing a larger magnitude current, see below, FIGS. 8-11.

Figure 8:
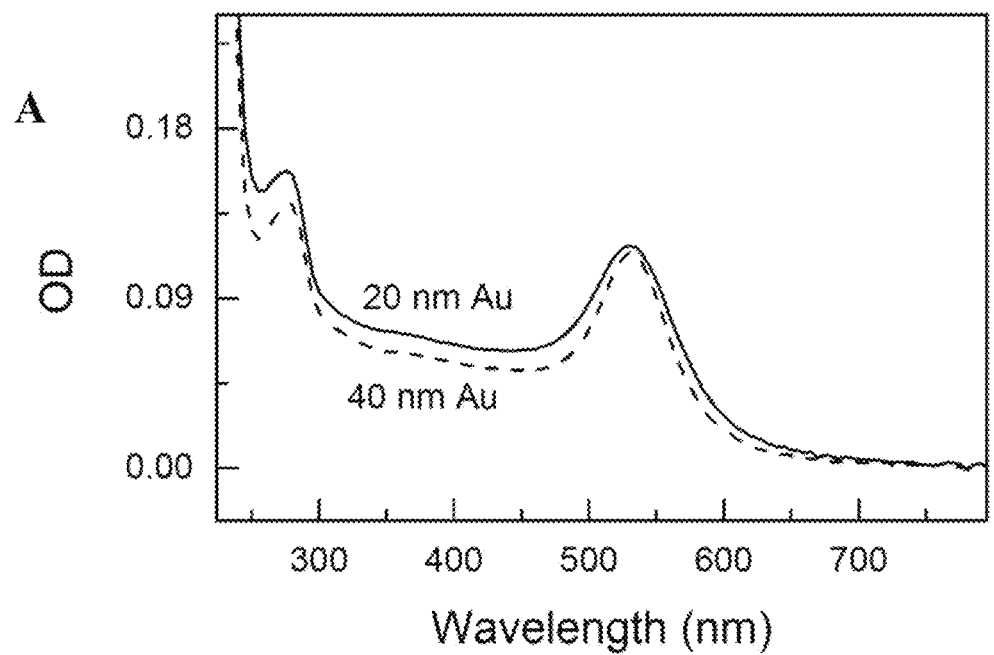
FIG. 8 shows the absorption spectra of 20 nm and 40 nm Gold conjugate anti-IgG (Rabbit). Insert: Graphical representation of the model immunological assay (IgG-anti-IgG) based on Plasmon Current (PC) upon light excitation. Ag—silver islands; Au—gold nanoparticle conjugated to anti-IgG.
Figure 8:
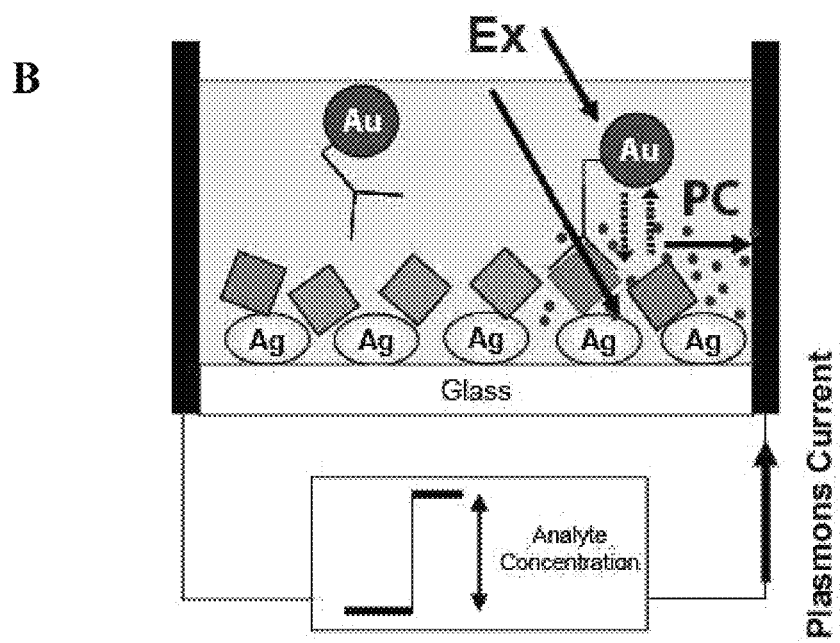
Figure 9:
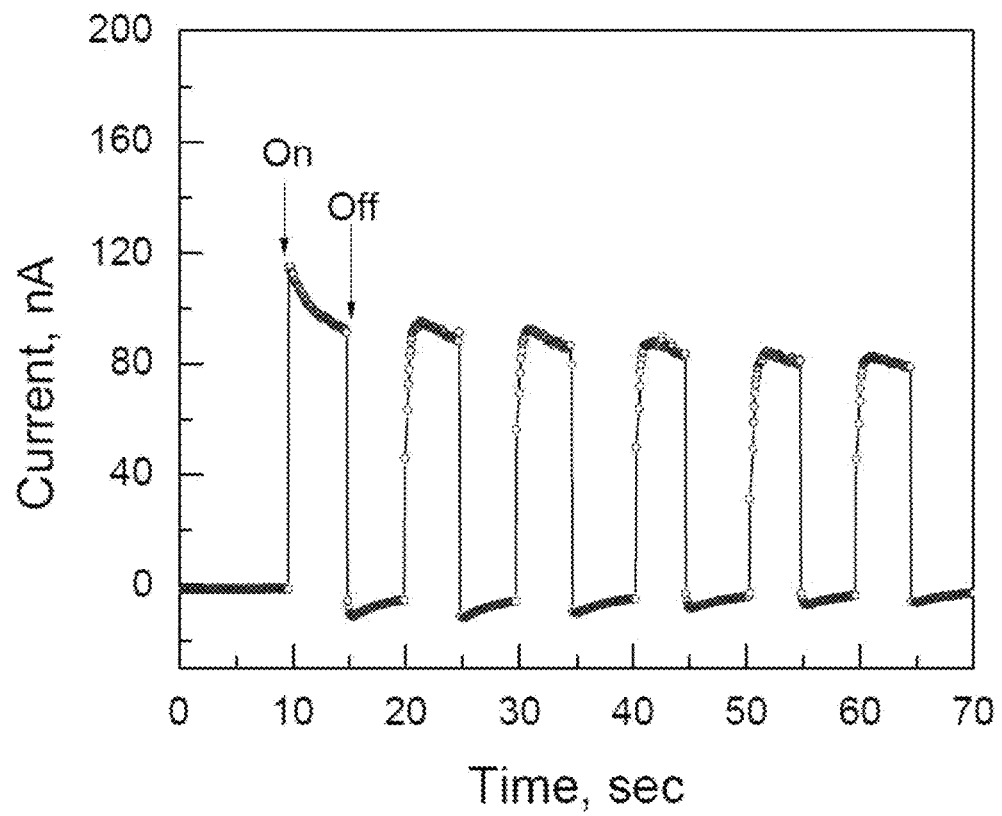
FIG. 9 shows current induced in SiF-IgG covered with 40 nm Gold conjugate anti-IgG. lex was 473 nm and the concentration of Gold—anti-IgG was 0.1 nM.
Figure 10:
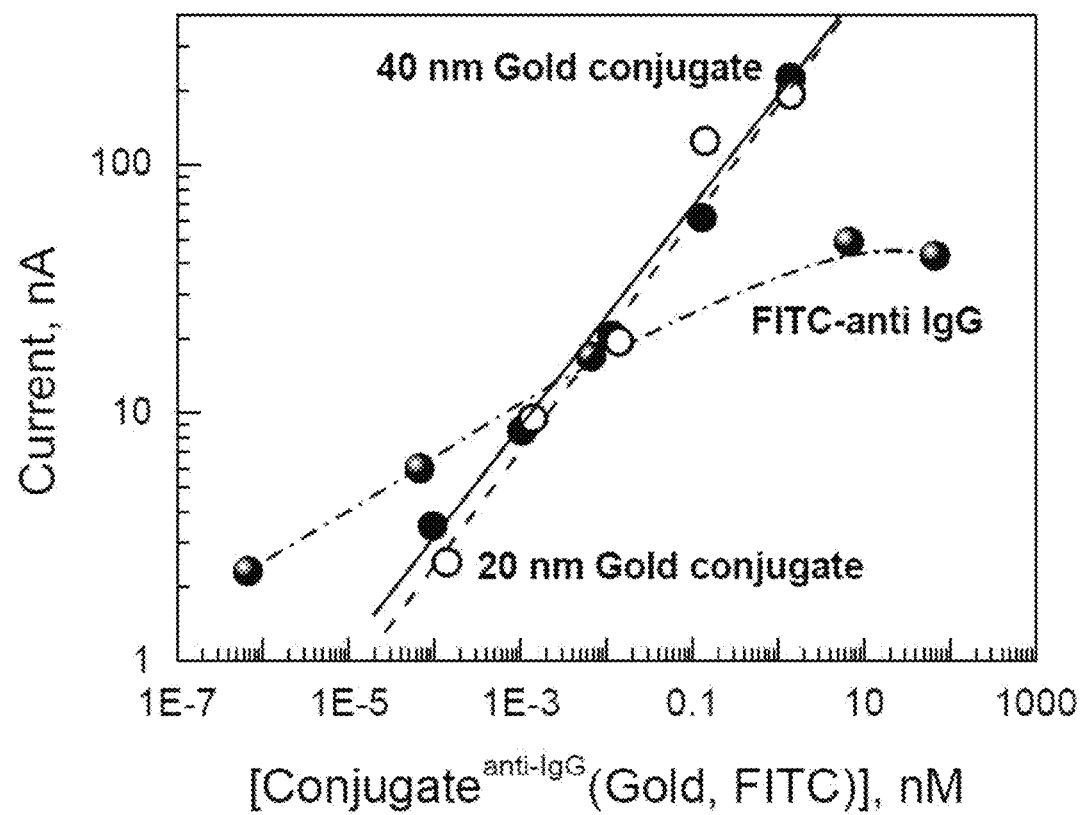
FIG. 10 shows the dependences of the current, induced by the 473 nm laser in SiF-IgG slides, upon concentration of anti-IgG conjugates (20 nm and 40 nm Gold, or FITC).
Figure 11:
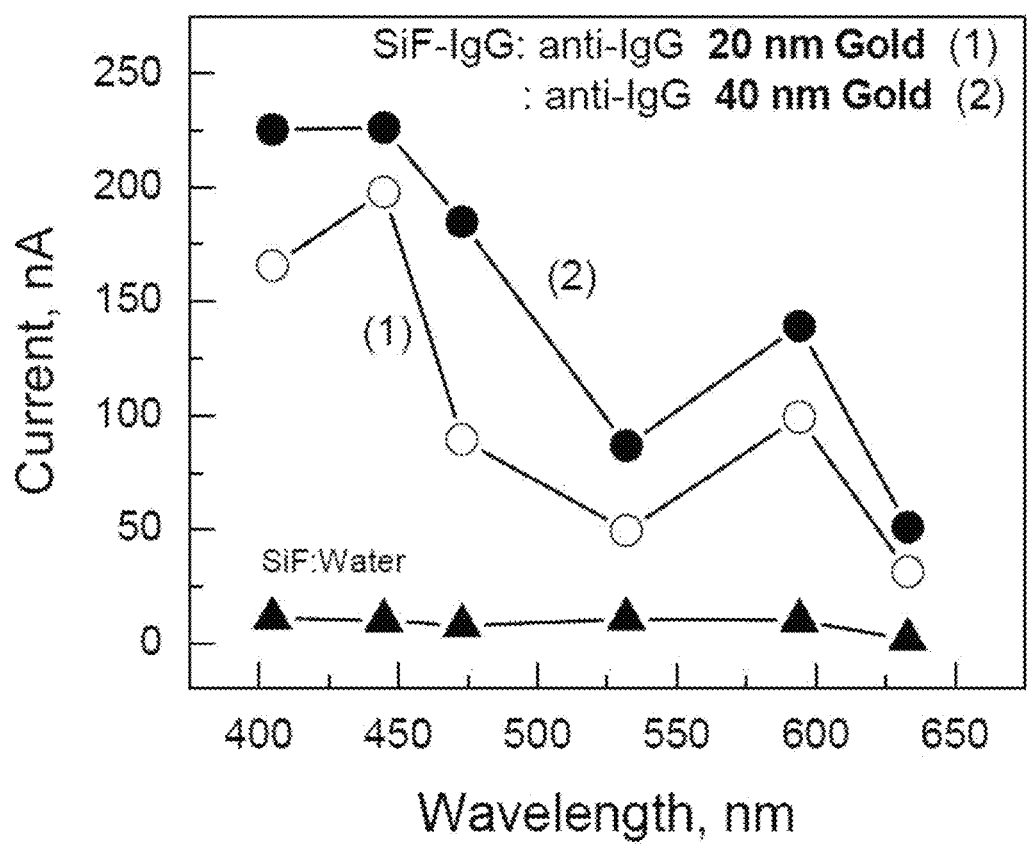
FIG. 11 shows the dependence of the current in SiF-IgG slides, coated with 20 nm and 40 nm. Gold conjugates anti-IgG, upon the wavelength of excitation. Laser powers were normalized to ≈45 mW.

Other Labels Besides Fluorophores can Cause Induced Current:

In addition to Fluorescent species, using non-fluorescent species have been considered as labels to induce current in metals. Nanoparticles such as those comprised of gold, silver, copper, platinum, also work, as shown in FIGS. 8-11. FIG. 8 shows the simple assay constructed using both 20 and 40 nm gold colloids labeled to an antibody, which binds to immobilized antigen on SiFs coated surface. The plasmon absorption spectra of the antibody gold conjugate is shown in FIG. 8. When excited with a 473 nm laser line, current is induced in the SiFs, as shown in FIG. 9. The current is gated with the on-off gating of the laser source, demonstrating that the effect is due to light on the assay substrate which has been incubated with gold-colloid labeled antibody. Remarkably, the induced current is more significant than the current induced by fluorophores in the same assay system, FIG. 10. This is due to the fact, that a bigger dipole moment is observed with the colloid label as compared to a fluorophore label at the same excitation wavelength. Interestingly, and similar to fluorophores, the wavelength dependence of the current is a function of the absorption spectra of both the colloid labels as well as the Sifs (Silver Island Films) themselves as shown in FIG. 11. Interestingly shorter wavelengths produce greater current which is thought to be due to the position of the SiFs Plasmon absorption maximum. It is evident that larger colloids induce larger currents and the water background is low compare to induced current from colloids. Maximum current is observed when the system is excited at the Plasmon absorption maximum of the surface, that being, the silver island surface. Due to the large induced current, the colloids are excellent as probes.

Figure 12:
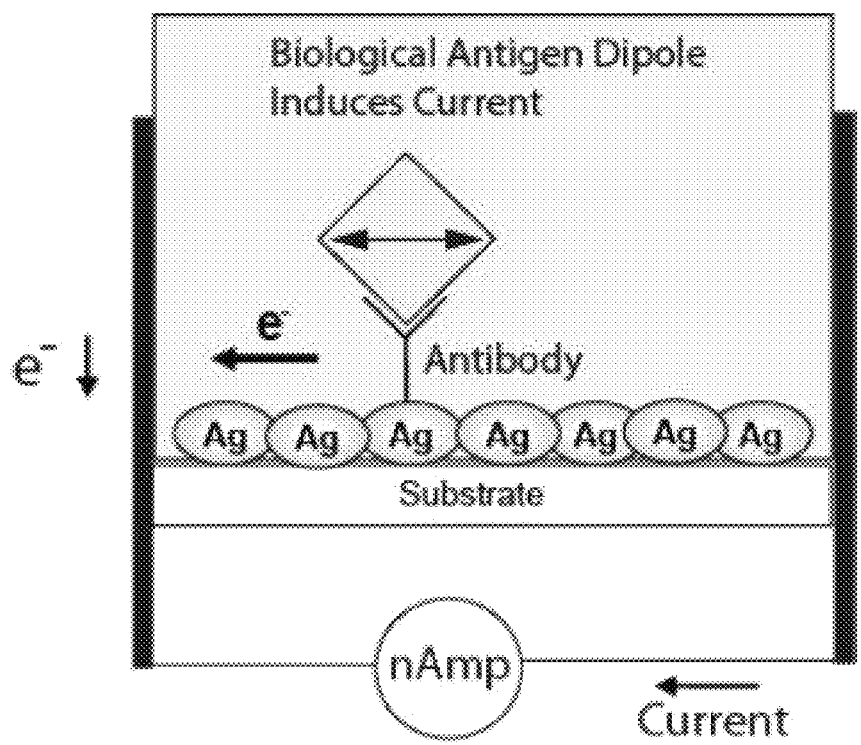
FIG. 12 shows the use of an antibody to detect a binding antigen wherein the binding antigen exhibits a dipole moment and induces dipole in the metallic particles thereby generating a current flow.
Figure 13:
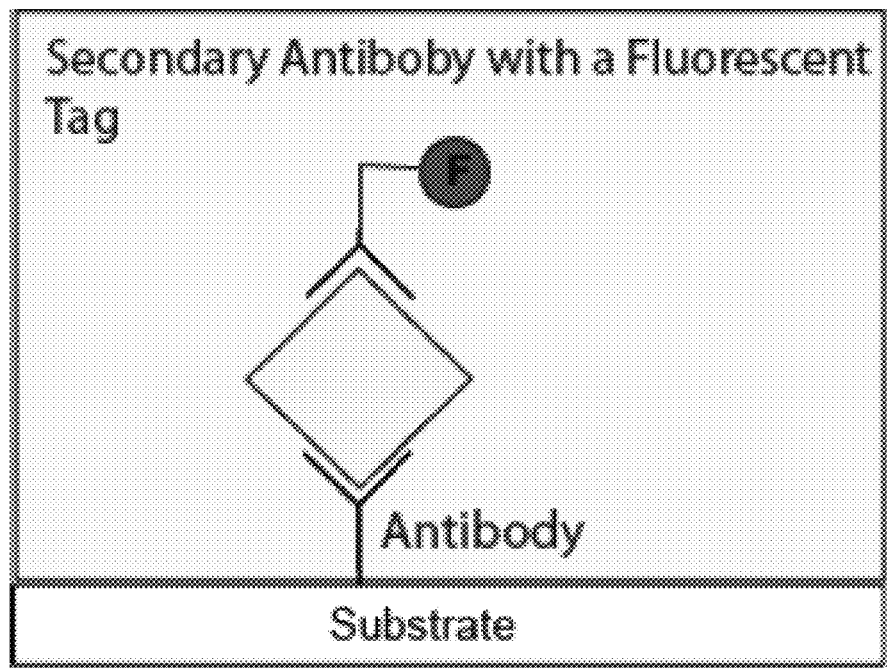
FIG. 13 shows the use of two antibodies wherein one captures the target antigen and the other provides for a fluorophore tag that upon excitation causes an induce dipole in the metallic material.

FIGS. 12 and 13 show the use of an antibody that has a dipole moment and has the ability to induce mirror dipole in the metallic particles. Notably many antigens only allow for a single antibody to bind to them so fluorescence is difficult to use for detection of these species. However, antibodies can be bound to surfaces for the capture of such antigens that has a dipole moment upon excitation can induce a dipole in the metallic material and thus induce a current. This will be very useful for applications where only one antibody can bind an antigen. A fluorophore can also be used as shown in FIG. 13.

Figure 14:
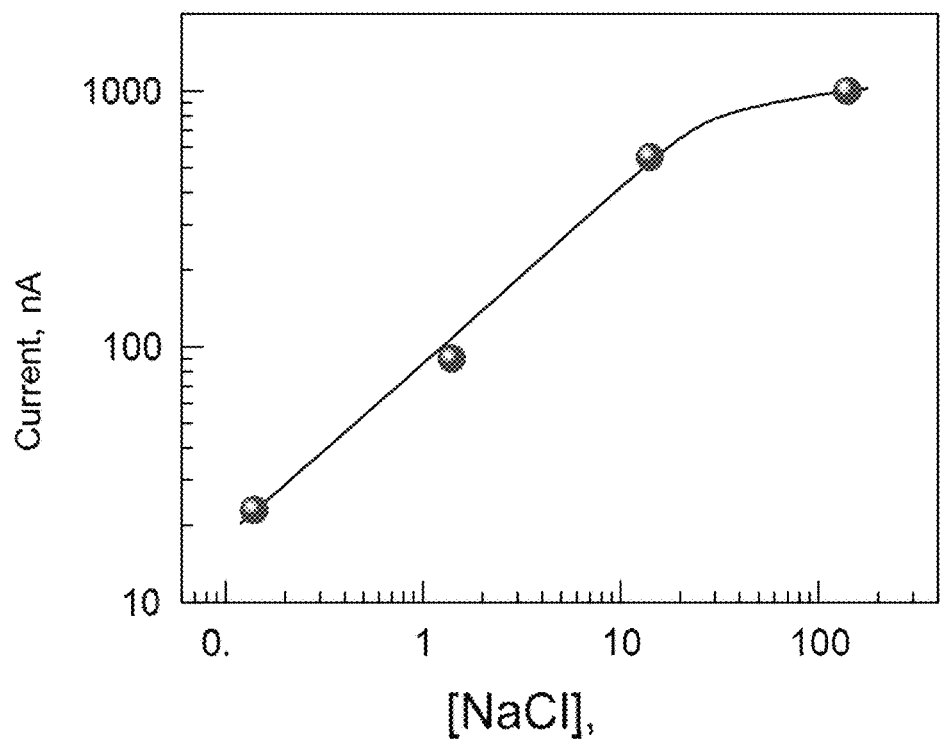
FIG. 14 shows that plasmonic current is dependent on the concentration of an electrolyte in solution. Current in SiF: solvent wa induced by 473 nm laser irradiation and the pH of the solution was constant at 7.4.
Figure 15:
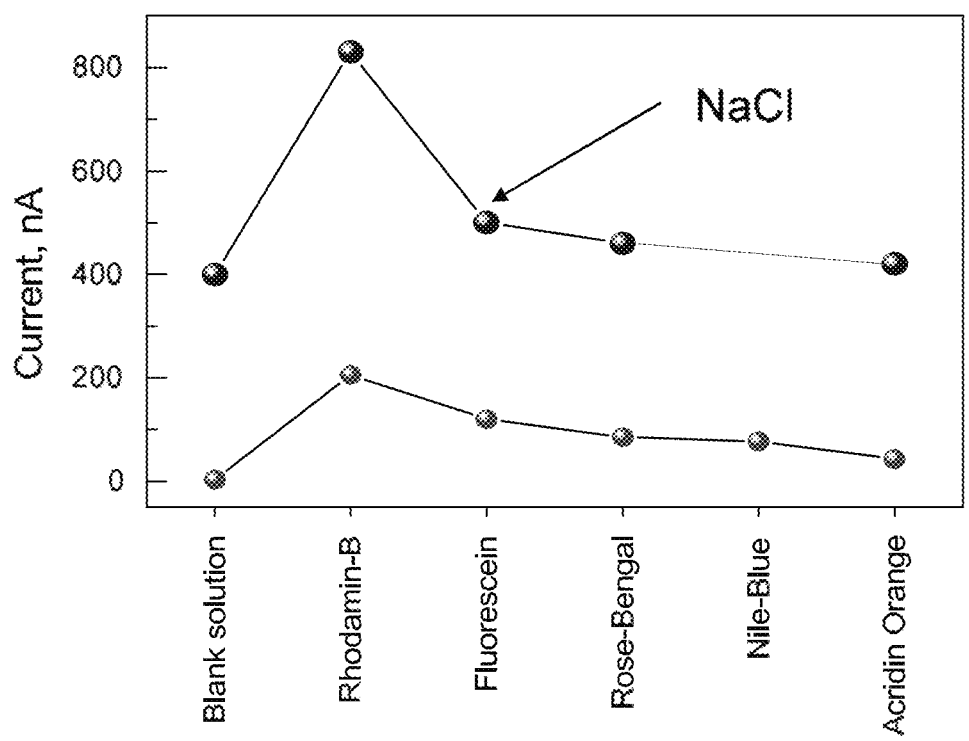
FIG. 15 shows plasmonic current induced by 473 nm laser radiation in SiFs covered with solutions the different dyes. Dyes were dissolved in water and in 70 mM NaCl.
Figure 16:
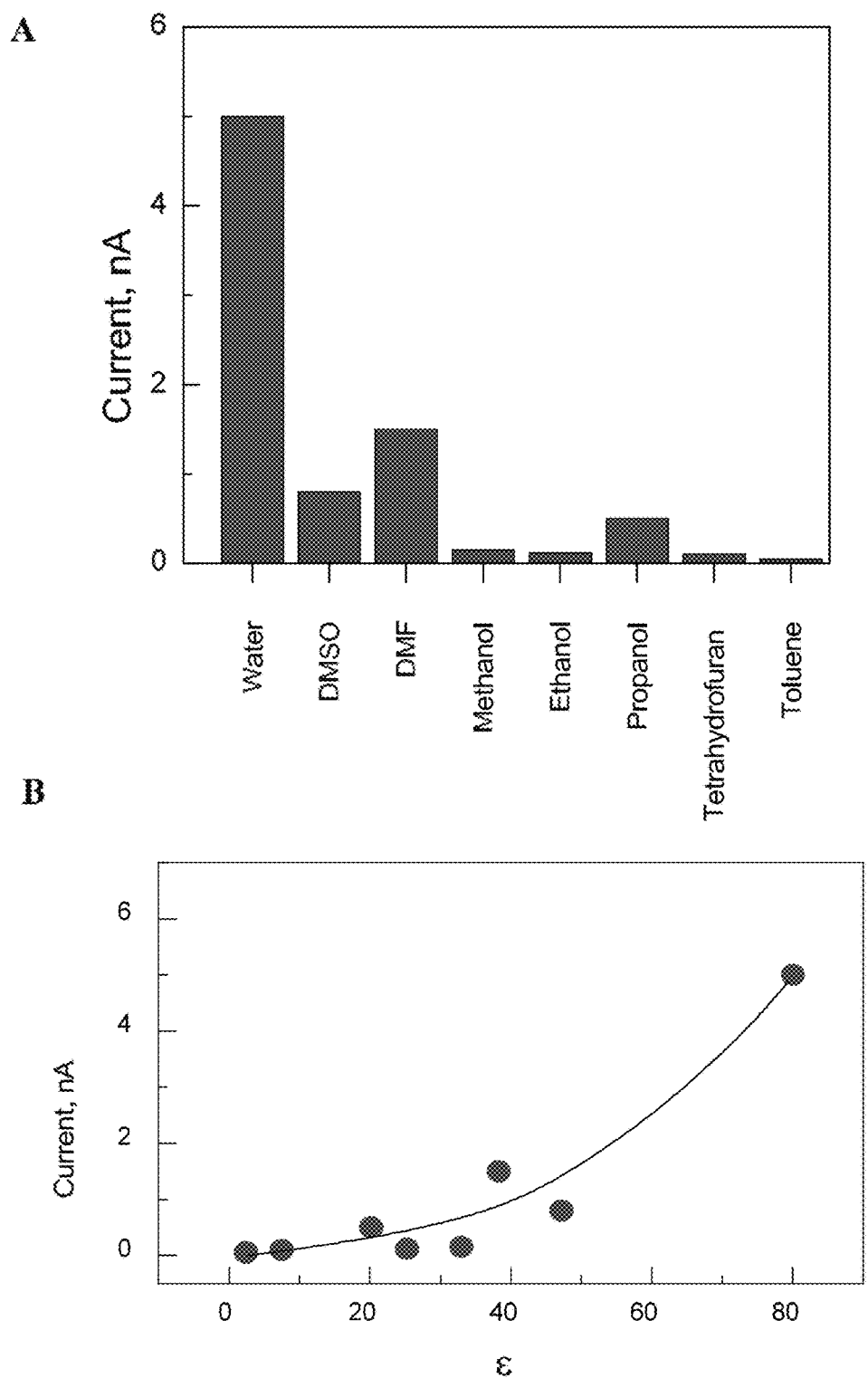
FIG. 16 shows that different solvents can induce the extent of the plasmonic current. The dielectric constants of the solvents Eincludes water 80, DMSO 46, DMF 36, Methanol 32, ethanol 24, propanol 20, Tetrahydrofuran 8, and Toluene 2.3.

FIG. 14 shows that plasmonic current can be dependent on solution salt concentration. As shown in FIG. 14, the current increases in the silver island films as the NaCl concentration increases. As shown in FIG. 15, dye produce much greater current by being dissolved in an aqueous solution have 70 mM of NaCl. Plasmonic current was readily detected in the presence of salt solutions which can be very effective in biological assays. Different solvents can also induce different levels of plasmonic current as shown in FIGS. 16 A and B. As the dielectric constant of the solvent increases, the observed current in the SiFs slide also increase as shown in FIG. 16B. Clearly water having a dielectric constant of about 80 induces the highest level of current.

Figure 17:
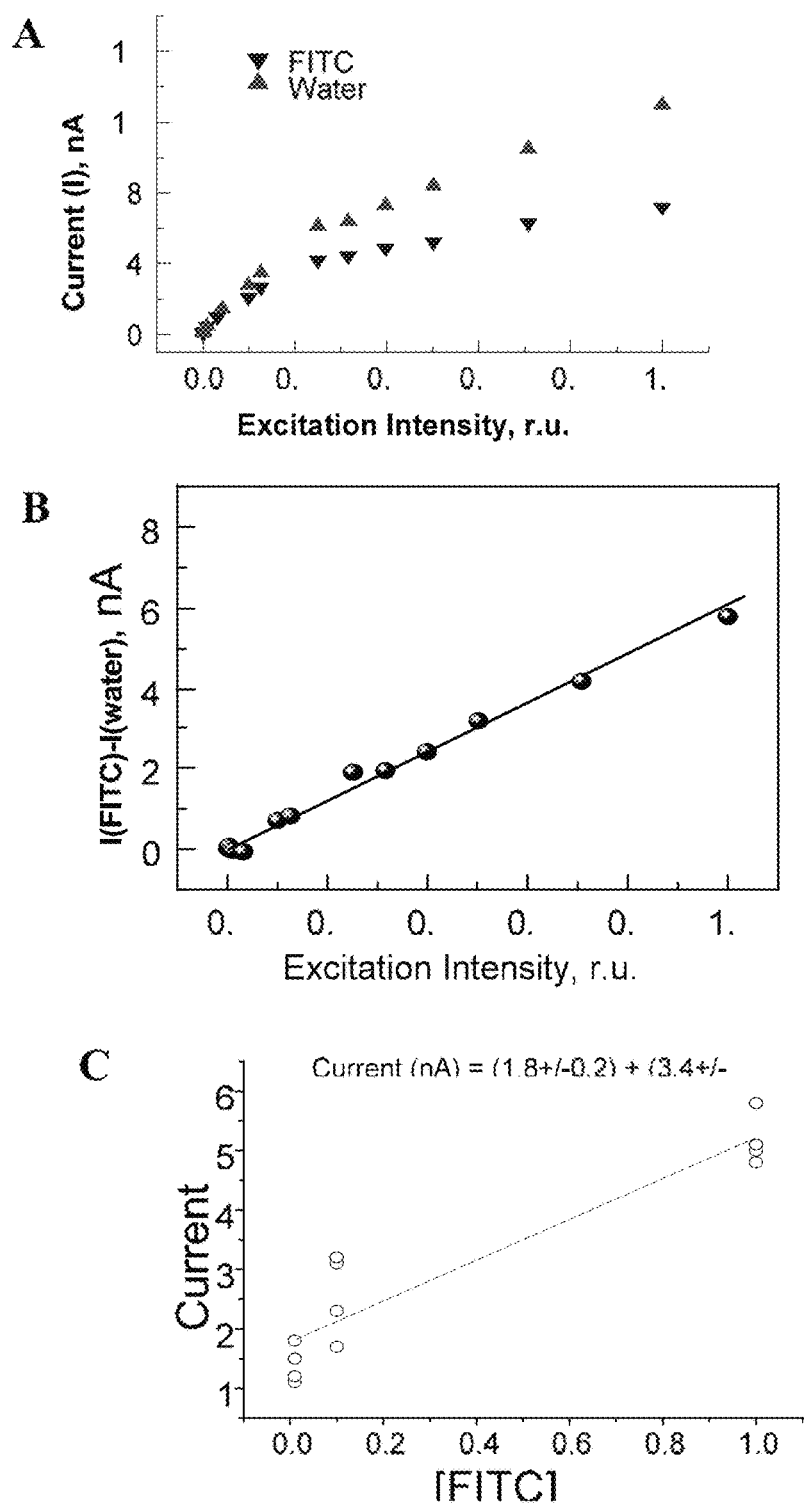
FIG. 17 shows that plasmonic current depends on both the incoming excitation intensity and also the concentration of the dye in solution. The current was induced buy a laser (473 nm wavelength and 500 mW.

FIG. 17 shows that plasmonic current depends on both the incoming excitation intensity and also the concentration of the dye in solution. Silver coated slides comprising the silver structures, spatially separated, were prepared and including FITC as the excitable molecule. It is evident that as the excitation intensity increases, the current also increases. Further the increase in FITC causes an increase in current. As such, as binding of FITC increase in a system due to increased binding of a target substance, then the methods and systems can be used for determining the amount of a target substance, wherein the amount of current is proportional to the binding amount of the target substance.

Figure 18:
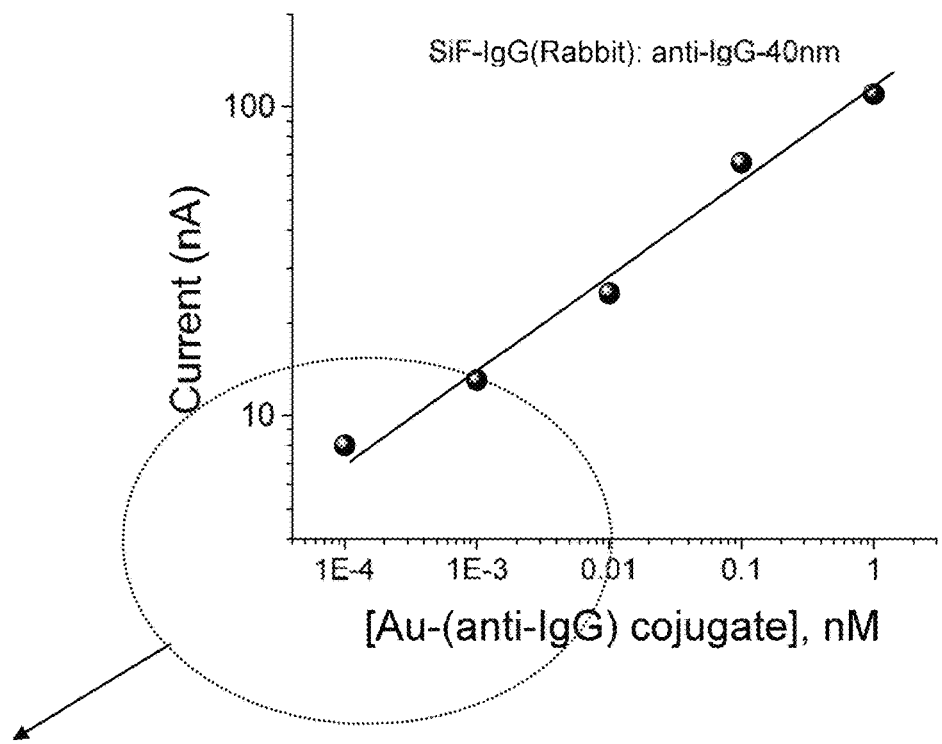
FIG. 18 shows that gold colloids can be used as excitable probes in immunoassays and provide a method of determining the amount of a target substance.

FIG. 18 shows a system wherein metallic gold probes are used as the excitable molecule in combination with silver structures immobilized on a substrate surface. Rabbit antibodies IgG are connected to the silver structures and then free anti-IgG is introduced for binding with the immobilized antibodies. The free antibodies are bound to or can be bound to gold colloids. As shown in FIG. 18, as the amount of gold colloids increases (increase of binding of free anti-IgG to immobilized IgG) the current increases and again this method can be used to quantitate a target substance.

Figure 19:
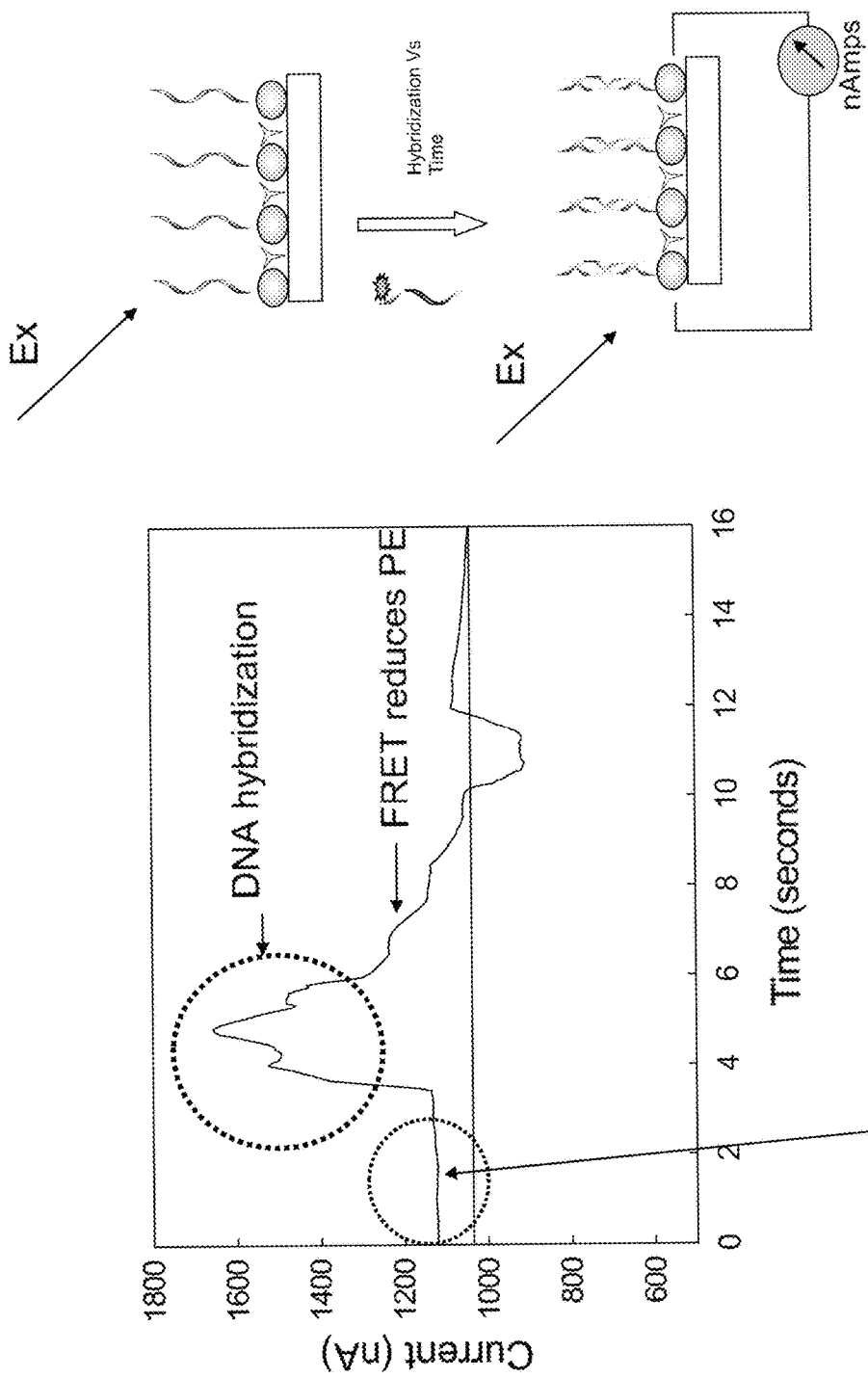
FIG. 19 shows that a hybridization process can be followed by the measurement of current produced during the process.

FIG. 19 provides results showing that a hybridization reaction can be followed and an indication as to when the hybridization is completed. This system includes silver structures immobilized on a substrate, wherein the substrate includes nucleotide primers for such hybridization. As the free nucleotides hybridize to the immobilized primers, the fluorophore is positioned at the correct distance from the silver structures and cause a current in the metallic structures. As shown in FIG. 19 as the hybridization process is ongoing, there is an increase in current and as the hybridization is completed, the current is reduced. Notably fluorescence resonance energy transfer (FRET) can also cause a reduction in the plasmonic electricity.

Figure 20:
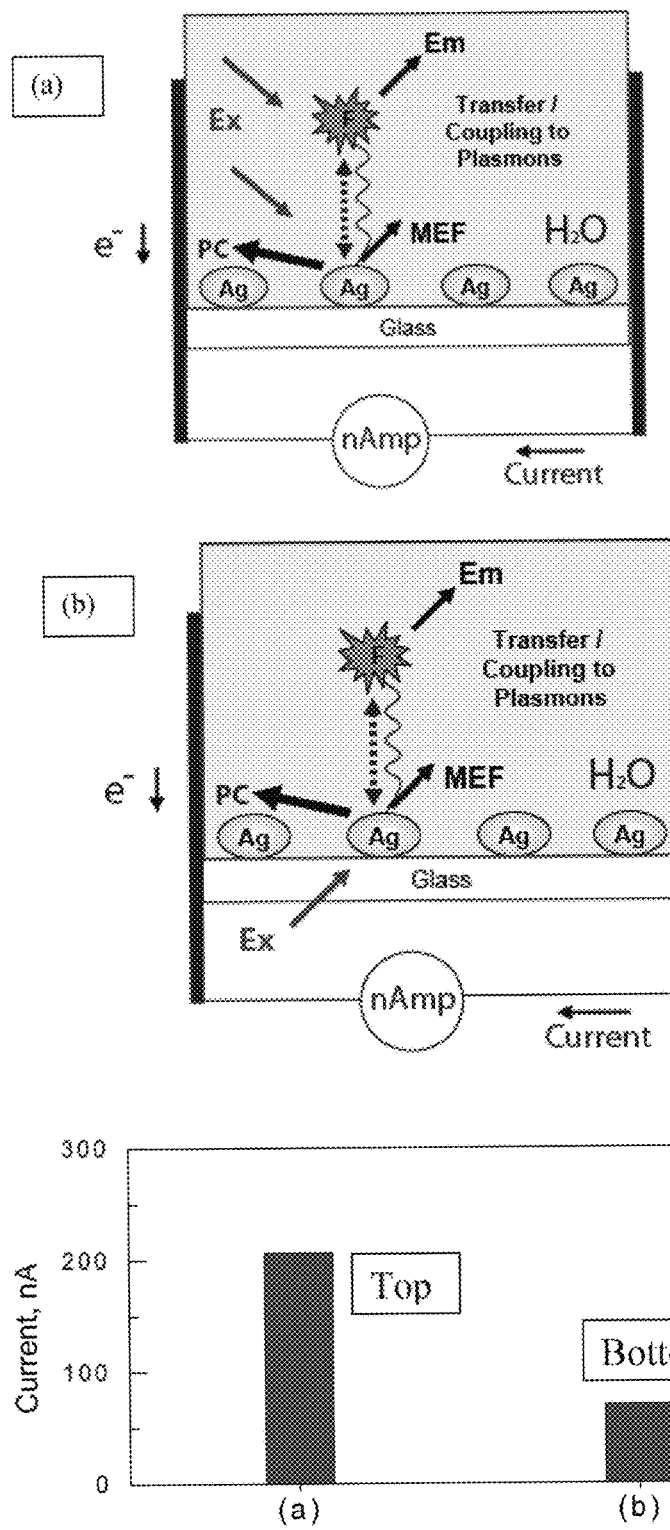
FIG. 20 shows that plasmonic current can be detected in various experimental geometries including excitation from both the top and bottom of the surfaces comprising metallic structures.

FIG. 20 shows that plasmonic current is induced in SiF:Rhodamine-B coupling pair by irradiation with 473 nm laser. The figures show the set up using silver metallic structure immobilized on a glass substrate in a solution that can conduct electrons. The fluorophore Rhodamine-B is coupled to the metallic structures and upon excitation, energy is transferred to the metallic surface and a current is induced.

Figure 21:
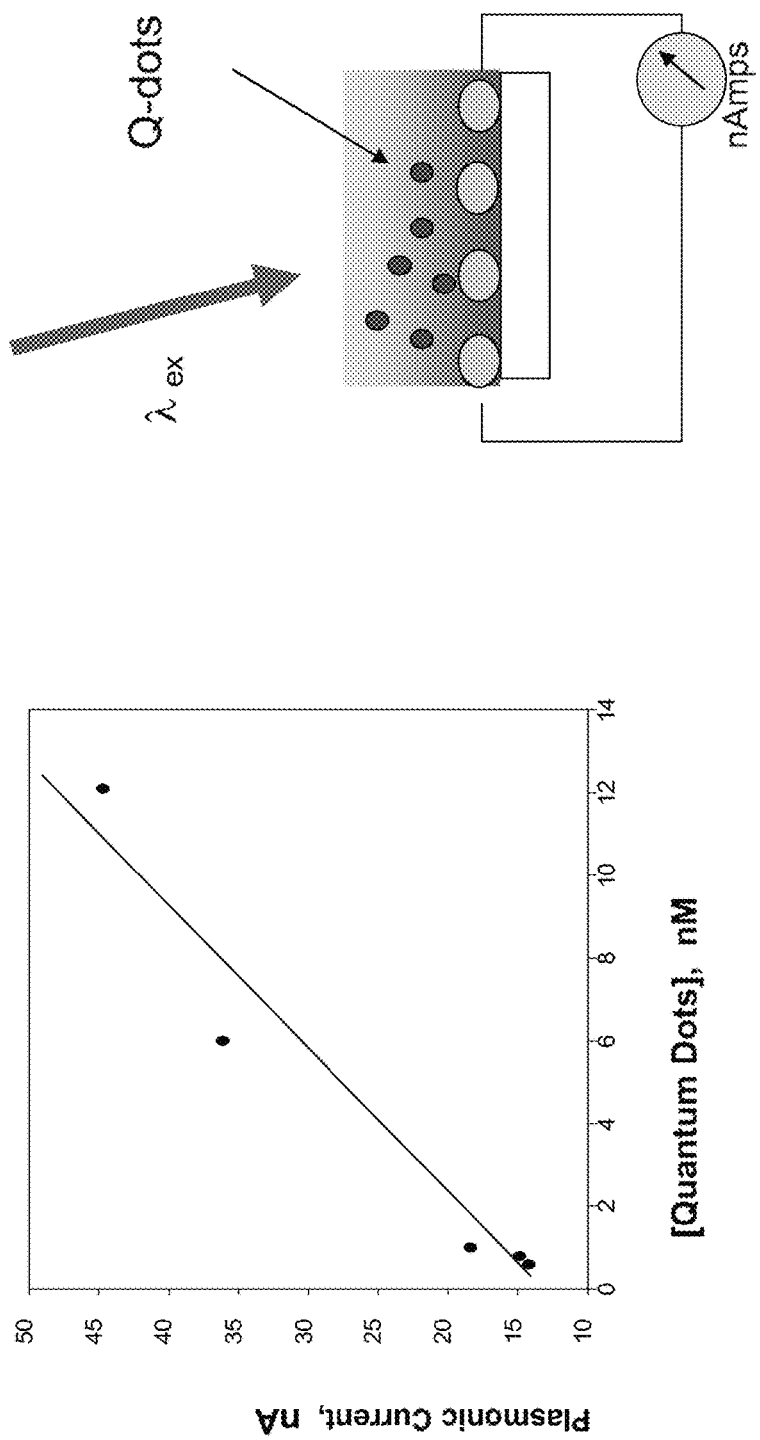
FIG. 21 shows that quantum dots can also induce plasmonic current when positioned near the metallic structures.

FIG. 21 shows that quantum dots acting as an excitable molecule can also induce a plasmonic current.

As shown above, the present invention provides for multiple uses of plasmonic electricity including:

As a direct measure of Fluorescence, phosphorescence or chemiluminescence signatures.
To provide digital read out of the above, without the need for additional analogue to digital conversion processes.
In immunoassays, as a direct measurement of surface analytes by measuring induced current and not fluorescence or another luminescence signature.
As a new class of detectors, directly converting fluorescence to electricity.
In solar powering devices, with or without fluorophores or other nanoparticle labels.
To enable immunoassays to be self powering away from a wall socket.
In multiplexed and high throughput screening applications.
As devices for converting light into electricity for electronic circuits.
In DNA assays, as a direct measure of a DNA hybridization event.
In RNA assays, to directly measure current from RNA assays, after hybridization.
In chemiluminescence assays, using Horse Radish Peroxidase substrates.
As a technology to measure distance of a fluorescence (or other dipole) from a metallic substrate.
In light emitting diode constructs.
As a technology for eliminating fluorescence detection optics in fluorescence based immunoassays, one simply measures the induced current and does not bother to measure the fluorescence using a different detector, optics and filters.
Conductive materials such as textiles used for charging or powering hand held devices, such as radios, ipods and communication devices.
Conductive textiles attached to a self cooling device or to provide for color alteration of the textile.

REFERENCES

The contents of all references cited herein are incorporated by reference herein for all purposes.

(1) Collings, F. B.; Vaidya, V. S. *Toxicology* 2008, 245, 167-174.
(2) Lalvani, A.; Meroni, P. L.; Millington, K. A.; Modolo, M. L.; Plebani, M.; Tincani, A.; Villalta, D.; Doria, A.; Ghirardello, A. *Clin Exp Rheumatol* 2008, 26, S62-66.
(3) Taipa, M. A. *Comb Chem High Throughput Screen* 2008, 11, 325-335.
(4) Enander, K.; Choulier, L.; Olsson, A. L.; Yushchenko, D. A.; Kanmert, D.; Klymchenko, A. S.; Demchenko, A. P.; Mely, Y.; Altschuh, D. *Bioconjug Chem* 2008.
(5) Schultz, E.; Galland, R.; Du Bouetiez, D.; Flahaut, T.; Planat-Chretien, A.; Lesbre, F.; Hoang, A.; Volland, H.; Perraut, F. *Biosens Bioelectron* 2008, 23, 987-994.
(6) Matveeva, E.; Gryczynski, Z.; Gryczynski, I.; Malicka, J.; Lakowicz, J. R. *Analytical Chemistry* 2004, 76, 6287-6292.
(7) Matveeva, E.; Malicka, J.; Gryczynski, I.; Gryczynski, Z.; Lakowicz, J. R. *Biochem Biophys Res Commun* 2004, 313, 721-726.
(8) Aslan, K.; Gryczynski, I.; Malicka, J.; Matveeva, E.; Lakowicz, J. R.; Geddes, C. D. *Current Opinion in Biotechnology* 2005, 16, 55-62.
(9) Aslan, K.; Lakowicz, J. R.; Szmacinski, H.; Geddes, C. D. *Journal of Fluorescence* 2005, 15, 37-40.
(10) Geddes, C. D.; Lakowicz, J. R. *Journal of Fluorescence* 2002, 12, 121-129.
(11) Aslan, K.; Geddes, C. D. *Analytical Chemistry* 2005, 77, 8057-8067.
(12) Aslan, K.; Zhang, Y.; Hibbs, S.; Baillie, L.; Previte, M. J.; Geddes, C. D. *Analyst* 2007, 132, 1130-1138.
(13) Aslan, K.; Holley, P.; Geddes, C. D. *Journal of Immunological Methods* 2006, 312, 137-147.
(14) Thornycroft, L. H.; Barnaby, S. W. *Min. Proc. Inst. Chem. Eng,* 1895, 122 51-69.
(15) Suslick, K. S. *Science* 1990, 247, 1439-1445.
(16) Gould, R. K.; Coakley, W. T.; Grundy, M. A. *Ultrasonics* 1992, 30, 239-244.
(17) Suslick, K. S.; Flannigan, D. J. *Annu Rev Phys Chem* 2008, 59, 659-683.
(18) Neppiras, E. A. *Phys. Rep.* 1980, 61, 159-251.
(19) Aslan, K.; Leonenko, Z.; Lakowicz, J. R.; Geddes, C. D. *Journal of Fluorescence* 2005, 15, 643-654.
(20) Lofas, S.; Malmqvist, M.; Ronnberg, I.; Stenberg, E.; Liedberg, B.; Lundstrom, I. *Sensors and Actuators B-Chemical* 1991, 5, 79-84.

That which is claimed is:

1. A system for generating electrical current, the system comprising:
    a substrate positioned on the bottom of a container comprising spatially separated immobilized metallic structures positioned on the substrate, wherein the metallic structures are shaped as particles, nanostructures, island or colloids, wherein the metallic structures are positioned a distance apart from about 10 to 50 nm, wherein the metallic structures and substrate within the container are covered with an aqueous solvent to increase current flow between the metallic structures;
    a set of electrically conductive electrodes communicatively contacting at least two of the metallic structures positioned thereon,
    an excitable probe positioned near the metallic structures, at a distance from about 10 nm to about 30 nm, wherein excitation of the excitable probe with electromagnetic energy induces a mirror dipole in the metallic material causing plasmonic current flow for storage or directing to a current reading device.

2. The system of claim 1, wherein the metallic structures are selected from the group consisting of silver, gold, platinum, zinc, aluminum, indium, palladium, rhodium iron, nickel, copper and combinations thereof.

3. The system of claim 1, wherein the electrodes are communicatively connected to the current reading device.

4. The system of claim 1, wherein the substrate is selected from the group consisting of glass, quartz, cellulose, a polymeric material and a combination thereof.

5. The system of claim 1, wherein electromagnetic energy source is positioned a distance from the first or second electrode to increase current to be detected by the current reading device.

6. The system of claim 1, wherein the plasmonic current flow is proportional to the amount of binding fluorophores.

7. The system of claim 1, wherein the conductive solvent is a polar solvent or a dipolar aprotic solvent.

8. The system of claim 1, wherein the excitable probe emits fluorescence, luminescence, or phosphorescence signatures.

9. The system of claim 1 used in immunoassays, hybridization assays, resonance energy transfer assays, polarization/anisotropy based assays, chemiluminescence based assays, luminescence based assays, or enzyme-linked immunosorbent assays.

10. The system of claim 1, wherein the immobilized metallic structures further comprise a binding receptor for capturing a targeted substance.

11. The system of claim 1, wherein the substrate is within a container and the electrodes are positioned within the solvent.

12. The system of claim 1, wherein the current reading device is an ampmeter.

13. A method of generating electrical current comprising:
   providing a system according to claim 1;
   exciting the excitable probe with an electromagnetic source to cause the dipole moment and whereby such excitement induces a dipole in the metallic structures thereby causing plasmonic current flow;
   measuring the plasmonic current flow.

14. The method of claim 13, wherein the metallic structures are selected from the group consisting of silver, gold, platinum, zinc, aluminum, indium, palladium, rhodium iron, nickel, copper and combinations thereof.

15. The method of claim 13, wherein the electrodes are communicatively connected to the current reading device.

16. The method of claim 13, wherein the substrate is selected from the group consisting of glass, quartz, cellulose, a polymeric material and a combination thereof.

* * * * *